United States Patent
De Paepe et al.

(10) Patent No.: US 11,472,790 B2
(45) Date of Patent: Oct. 18, 2022

(54) DINITROXIDE BIRADICAL COMPOUNDS AS POLARIZING AGENTS

(71) Applicants: COMMISSARIAT A L'ENERGIE ATOMIQUE ET AUX ENERGIES ALTERNATIVES, Paris (FR); UNIVERSITY OF ICELAND, Reykjavik (IS)

(72) Inventors: Gaël De Paepe, Voiron (FR); Frédéric Mentink-Vigier, Aigues Mortes (FR); Snorri Sigurdsson, Reykjavik (IS); Anil Jagtap, Maharashtra (IN)

(73) Assignees: COMMISSARIAT A L'ENERGIE ATOMIQUE ET AUX ENERGIES ALTERNATIVES, Paris (FR); University of Iceland, Reykjavik (IS)

( * ) Notice: Subject to any disclaimer, the term of this patent is extended or adjusted under 35 U.S.C. 154(b) by 13 days.

(21) Appl. No.: 16/628,207

(22) PCT Filed: Jul. 3, 2018

(86) PCT No.: PCT/EP2018/068002
§ 371 (c)(1),
(2) Date: Jan. 2, 2020

(87) PCT Pub. No.: WO2019/007989
PCT Pub. Date: Jan. 10, 2019

(65) Prior Publication Data
US 2020/0148666 A1 May 14, 2020

(30) Foreign Application Priority Data
Jul. 5, 2017 (EP) .................................... 17179869

(51) Int. Cl.
*C07D 401/12* (2006.01)
*C07F 9/6561* (2006.01)
*G01R 33/56* (2006.01)
*G01R 33/46* (2006.01)

(52) U.S. Cl.
CPC .......... *C07D 401/12* (2013.01); *C07F 9/6561* (2013.01); *G01R 33/5601* (2013.01); *G01R 33/46* (2013.01)

(58) Field of Classification Search
CPC ................................................. C07D 401/12
USPC ........................................................... 546/23
See application file for complete search history.

(56) References Cited

U.S. PATENT DOCUMENTS 7,985,594 B2 * 7/2011 Griffin ................. C07D 401/12
436/173
9,738,657 B2 * 8/2017 Sauvee ................ C07D 401/12

FOREIGN PATENT DOCUMENTS

| EP | 2 789 609 A1 | 10/2014 |
| GB | 2 001 771 A | 2/1979 |
| WO | 2008/048714 A2 | 4/2008 |

OTHER PUBLICATIONS

Mentink-Vigier, J. Am. Chem. Soc. 2018, 140, 11013-1101.*
Blaquiere, Journal of Molecular Structure (1986), 144(3-4), 377-9.*
Ysaco, Physical Chemistry Chemical Physics 12(22):5841-5845, 2010.*
Vlaera, Journal of Organic Chemistry 79:8313-8323, 2014.*
Becker, Russian Chemical Bulletin 56:1210-1215, 2007.*
Kubicki, Chemical Science (2016), 7(1), 550-558.*
Jagtap, Chemical Communications (Cambridge, United Kingdom) (2016), 52(43), 7020-7023.*
Becker, C.S., et al., "Transformations of Conjugated Enamines of the Imidazolidine 1-Oxide Series in the Vilsmeier-Haack Reaction," Russian Chemical Bulletin 56:1210-1215, 2007.
Blaquiere, C., "ESR Study of Nitroxide Biradicals," Journal of Molecular Structure 144(3-4):377-379, May 1986.
Valera, S., et al., "A Modular Approach for the Synthesis of Nanometer-Sized Polynitroxide Multi-Spin Systems," Journal of Organic Chemistry 79:8313-8323, 2014.
Ysacco, C., et al., "Properties of Dinitroxides for Use in Dynamic Nuclear Polarization (DNP)," Physical Chemistry Chemical Physics 12(22):5841-5845, 2010.
International Search Report dated Aug. 30, 2018, issued in corresponding International Application No. PCT/EP2018/068002, filed Jul. 3, 2018, 3 pages.

* cited by examiner

*Primary Examiner* — Nizal S Chandrakumar
(74) *Attorney, Agent, or Firm* — Christensen O'Connor Johnson Kindness PLLC

(57) ABSTRACT

The present invention relates to novel organic dinitroxide biradical compounds and their use as polarizing agents, in particular, in the techniques of Nuclear Magnetic Resonance (NMR) of solids or liquid samples and medical imaging.

8 Claims, 17 Drawing Sheets

DINITROXIDE BIRADICAL COMPOUNDS AS POLARIZING AGENTS

Figure 1:
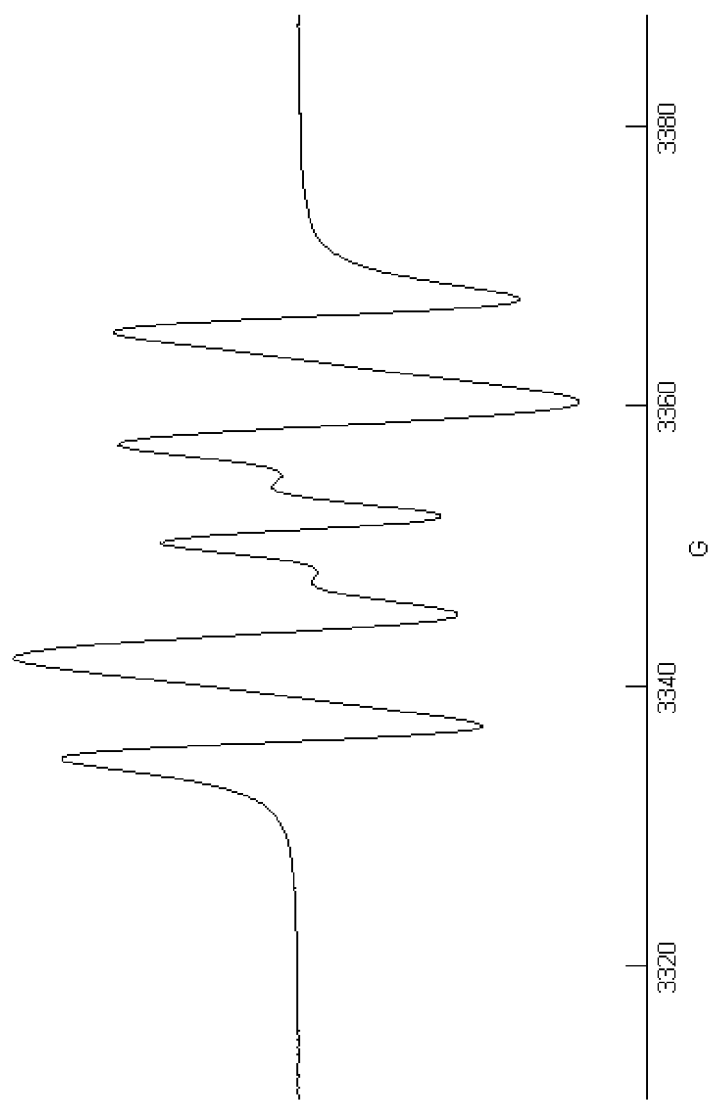

The present invention relates to novel organic dinitroxide biradical compounds and their use as polarizing agents, in particular, in the techniques of Nuclear Magnetic Resonance (NMR) of solids or liquid samples and medical imaging.

Nuclear magnetic resonance (NMR) is a very informative characterization method that allows probing matter by detecting signals of nuclear spins placed in a sufficiently stable, homogeneous and intense magnetic field (up to tens of Tesla typically). This technique makes it possible to record spectral data which, once interpreted, provide information at the atomic scale on the structure and the dynamics of the system studied. The use of NMR is widespread in chemistry, biology and materials science.

Several classes of NMR experiments have been developed over the years. Static solid-state NMR which stands for experiments conducted on static sample holders, often filled with oriented samples. Magic Angle Spinning (MAS) solid-state NMR refers to experiments conducted on spinning samples. This approach is based on the pneumatic rotation of the sample in order to induce a spatial averaging of anisotropic interactions. The axis of the rotation often corresponds, but not limited to, a precise orientation with respect to the magnetic field called "magic angle". Another class of experiments involve the detection of liquids and is broadly referred to solution-state NMR. Finally, experiments aiming at performing imaging are referred to Magnetic Resonance Imaging (MRI).

NMR detection offers a lot of information but suffers from a lack of sensitivity in comparison with other analytical techniques. The acquisition of signals of interest is therefore often long and/or requires the use of important amount of material. This limitation is inherent to the properties of the nuclei, which are said to have a small polarization under standard experimental conditions. This lack of sensitivity undoubtedly limits the use of NMR for the development of new materials (for catalysis, energy storage and conversion, etc.), as well as its impact in biology and health related challenges.

To compensate for this lack of sensitivity, a technique of hyperpolarization, called dynamic nuclear polarization (DNP), can be used. This phenomenon, discovered in 1953 on conductive materials using weak magnetic fields, has gradually became a very active field of research over the last decades, after it was shown that this hyperpolarization step could be combined with contemporary magnetic fields (3 T-20 T and higher). The main two approaches are called "dissolution DNP" and "solid-state DNP". The former polarizes the sample in the solid-state (often at very low temperature) and is followed by a sample melting step, before NMR detection in the liquid state. The later polarizes the sample in the solid-state, and perform the NMR detection in the solid-state as well, with static or spinning samples.

The development of solid-state DNP towards higher magnetic field, while keeping high resolution conditions (MAS), was pioneered in the group of Prof. Griffin at MIT. Thanks to major instrumental and theoretical developments, including access to high-power and high-frequency microwave sources, dynamic nuclear polarization applied to solid-state nuclear magnetic resonance appears as a promising solution for significantly increasing nuclear magnetization in many systems. This approach makes it possible to record new type of data and thus, obtain structural characteristics hitherto inaccessible. Currently, DNP (under MAS) measurements are typically performed at magnetic fields of about 1 to 20 Tesla, and, in most cases, require measurements at low temperature about 100 K). The measurements are carried out in sample holders (rotors) with a capacity of 1-100 µl.[1]

In high magnetic field DNP experiments, the systems of interest are generally dissolved, suspended or impregnated with a solution containing polarizing agents. This solution is typically chosen as a function of the system to be studied, and for its specific characteristics in terms of DNP efficiency (quality of the glass formed at low temperature, relaxation time of nuclear and electronic spins). The polarizing agent molecules contain paramagnetic centers with unpaired electrons, which give them an electron spin, about 660 times more polarized than a nuclear proton spin. The application of a suitable microwave irradiation makes it possible to transfer the magnetization of the electronic spins to the surrounding nuclear spins and, thus, to significantly increase the detected NMR signal.

Numerous polarizing agents have been developed over the years in order to optimize the signal-to-noise increase obtained by DNP. Several DNP mechanisms under rotation at the magic angle and high magnetic field have been described to date (K. R. Thurber and R. Tycko, "Theory for cross effect dynamic nuclear polarization under magic-angle spinning in solid state nuclear magnetic resonance: the importance of level crossings," *J. Chem. Phys.*, vol. 137, no. 8, pp. 84508, August 2012; F. Mentink-Vigier, U. Akbey, Y. Hovav, S. Vega, H. Oschkinat, and A. Feintuch, "Fast passage dynamic nuclear polarization on rotating solids," *J. Magn. Reson.*, vol. 224, pp. 13-21, November 2012). Among these different mechanisms, "Cross-Effect" (CE) combined with the use of biradicals as polarizing agents is currently the most promising in terms of sensitivity.

The modalities for the transfer of the polarization of the electrons towards the nuclei depend on the nature of the paramagnetic centers used. The objective is to maximize the polarization transfer while minimizing the time for such transfer under general experimental conditions: in the presence of a strong magnetic field, and/or rapid rotation of the sample. There are several magnetization transfer mechanisms under MAS, such as "Solid-Effect" (SE), "Cross-Effect" (CE) and "Overhauser Effect" (OE).

Under MAS-DNP experimental conditions as of today, which correspond to a magnetic field of about 5 to 20 T (or more), a sample rotation in the 1-40 kHz frequency range (or more), and a temperature of about 100 K, the CE is currently the method that offers the best results for DNP experiments under MAS. This type of experiment usually involves the use of polarizing agents that typically contain two paramagnetic centers, for example, two nitroxide entities bound by a bridge. This bridge, which ensures a substantial interaction between the electronic spins, is necessary for the CE mechanism. This interaction (dipole or J-exchange interaction) must be significant but not exceed the Larmor frequency of the targeted nucleus, as too much coupling leads to a loss of efficiency of the mechanism.

The distance between the electronic spins, and therefore the coupling, is not the only important criterion for optimizing the polarization gain. Like any paramagnetic center the magnetic properties of an unpaired spin are characterized by a g-tensor which relates to the molecular structure. In order for the CE to be active, it is also necessary for the planes defined by the nitroxide entities not to be parallel, in other words that the g-tensors are not collinear. The electron spin relaxation times ($T_{1e}/T_{2e}$) are also important parameters, as well as the nuclear spin density (e.g. protons), the hyperfine couplings and the associated relaxation times (in the absence/presence of paramagnetic doping). Ultimately, it is a complex set of parameters that governs the effectiveness of a DNP experiment.

The molecules most commonly used correspond to bi-nitroxide biradicals (TOTAPOL, the bTbK family, the bTUrea family) or mixed radicals (Tempo-Trityl and Tempo-BDPA). One of the first examples of binitroxides for DNP applications was: 1-(TEMPO-4-oxyl)-3-(TEMPO-4-amino)-propan-2-ol (TOTAPOL)

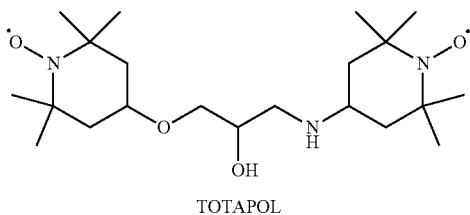

TOTAPOL which is compatible with experiments in aqueous media, including salt solutions commonly used in the study of proteins and nucleic acids. (C. Song, K.-N. N. Hu, C.-G. Joo, T. M. Swager, R. G. Griffin, J. Am. Chem. Soc., vol. 128, no. 35, pp. 11385-90, September 2006), and the bTUrea (bis-TEMPO-Urea) family

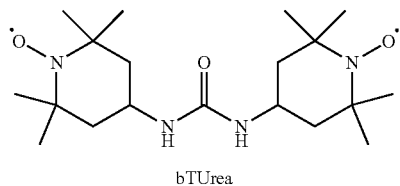

bTUrea (C. Sauvee, G. Casano, S. Abel, A. Rockenbauer, D. Akhmetzyanov, H. Karoui, D. Siri, F. Aussenac, W. Maas, R. T. Weber, T. Prisner, M. Rosay, P. Tordo, O. Ouari, Chem.—A Eur. J., vol. 22, no. 16, pp. 5598-5606, April 2016), in which link units connecting the nitroxide units are an ethylene glycol unit and a urea bridge, respectively. Note that the use of such bridge in bTUrea has reduced the distance between the electronic spins and rigidified the molecule i.e. the relative orientation of the nitroxide plans, as compared to the TOTAPOL case. Consequently, the interaction between the nitroxides is stronger and their relative orientation better defined, contributing to an increase of the DNP efficiency, which is consistent with the simulations recently reported (F. Mentink-Vigier, U. Akbey, H. Oschkinat, S. Vega, A. Feintuch, J. Magn. Reson., vol. 258, pp. 102-120, September 2015).

In parallel, another family of polarizing agents was introduced: the bTbK family, for which the linking motif is a ketal bridge.

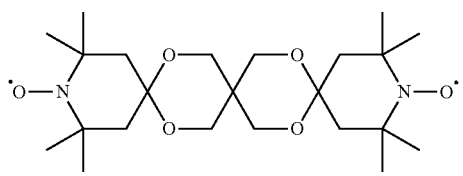

This ketal bridge imparts a great rigidity to the molecule and fixes almost totally the relative orientation of the two nitroxides and their associated g tensors. It is of note that this relative orientation is considered in the literature as close to the ideal solution. (Y. Matsuki, T. Maly, O. Ouari, H. Karoui, F. Le Moigne, E. Rizzato, S. Lyubenova, J. Herzfeld, T. F. Prisner, P. Tordo, R. G. Griffin, Angew. Chem. Int. Ed. Engl., vol. 48, no. 27, pp. 4996-5000, January 2009).

At this stage, it is important to note that the polarizing agents developed up to now are evaluated by measuring the ratio of the signal with and without microwave irradiation as well as the rise time in polarization.

The polarizing agents proposed up to now offer modest performances when the magnetic field is >9 T and/or the MAS frequency is >10 kHz. Their performance drops significantly at higher magnetic field, due to lower polarization gain and slower polarization speed (at higher magnetic field).

It is of high interest to develop new polarizing agents with new types of chemical bridges that will enhance the polarization transfer while minimizing the time for such transfer. Therefore, there is a real need for new polarizing agents having a chemical bridge that combines both a strong interaction between the electronic spins, a good relative orientation, interesting relaxation properties while maintaining good solubility in a DNP-compatible solvent and compatible with the intended application.

The present invention addresses these needs among others by providing compounds of formula (I)

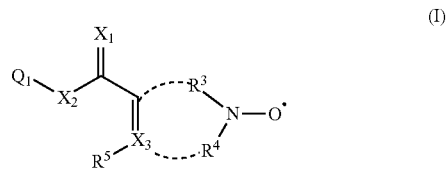

(I)

wherein $X_1$ is O, $C(R^6R^7)$, $NR^8$, S;

$X_2$ is O, $SO_2$, or $-NR^9$, $CH_2$;

$X_3$ is C or N with the proviso that when $X_3$ is N, then $R^5$ is not present in the molecule;

$R^5$, $R^6$, $R^7$, $R^8$ and $R^9$ are, independently, H; a substituted or unsubstituted, linear, branched or cyclic $C_{1-6}$ aliphatic group; $-(CH_2)_n-COOH$ with n being an integer from 1 to 10, $-OH$, $-NH_2$, $-N_3$, $-C\equiv CH$, $P(O)(OH)_2$, $P(O)(OR^{11})_2$, $P(O)R^{11}_2$, $-SSO_2Me$, $-(CH_2-CH_2-O)_m-CH_3$ or $-(CH_2-CH_2-O)_m-H$ with m being an integer from 1 to 500, preferably from 1 to 100, more preferably from 1 to 10, or

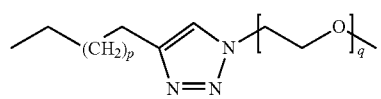

with p being an integer from 0 to 7 and q an integer from 1 to 500;

$Q_1$ is a cyclic or acyclic nitroxide radical, as represented below

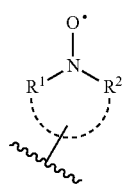

wherein
- $R^1$ and $R^2$ are, independently, a substituted or unsubstituted, linear, branched or cyclic $C_{1-6}$ aliphatic group; a substituted or unsubstituted linear, branched or cyclic hetero-aliphatic group comprising 5 carbon atoms and one heteroatom or heteroatomic group, respectively, selected from O, S, —$NR^{10}$—, $P(O)(OR^{11})$ and $P(O)(R^{11})$ substituted or unsubstituted aryl; substituted or unsubstituted heteroaryl, or substituted or unsubstituted 2,2,7,7-tetramethyl isoindolinoxyl, or substituted or unsubstituted 2,2,7,7-tetraethyl isoindolinoxyl; or
- $R^1$ and $R^2$ are joined, as indicated by ⌣⌣ to form together with the nitrogen atom to which they are bound a 5- to 8-membered heterocyclic ring and which may contain an additional heteroatom or heteroatomic group selected from $P(O)(OR^{11})$, $P(O)(R^{11})$, O, S, $N^+$—$O^-$, NH, $N(C_1-C_6$ alkyl) wherein the alkyl is straight, branched or cyclic, wherein the heterocyclic ring bears from one substituent to the maximum number of substituent on the carbon atoms and optionally contains one double bond; and
  with the proviso that the two groups $R^1$ or $R^2$ together do not contain more than one hydrogen alpha to the (N—O.) group;
- $R^{10}$ is hydrogen, hydroxyl; substituted or unsubstituted linear, branched or cyclic $C_{1-6}$ alkyl; $C_{1-6}$ alkylcarbonyl; substituted or unsubstituted aryl sulfinyl; or substituted or unsubstituted aryl sulfonyl;
- $R^{11}$ is linear or branched $C_{1-18}$ alkyl, H or an alkali metal; and wherein the point of attachment of the $X_2$ atom by a single bond, as indicated by

is to a primary or secondary non-olefinic or aromatic carbon atom of either $R^1$ or $R^2$, or to a carbon atom of the 5- to 8-membered heterocyclic ring formed by the joining of $R^1$ and $R^2$;
- $R^3$ or $R^4$ is linked to the double bond C=$X_3$ in the compound of formula (I) as represented above, wherein $R^3$ and $R^4$ are, independently, a substituted or unsubstituted, linear, branched or cyclic $C_{1-6}$ aliphatic group; a substituted or unsubstituted linear, branched or cyclic hetero-aliphatic group comprising 5 carbon atoms and one heteroatom or heteroatomic group, respectively, selected from O, S, —$NR^{10}$—, $P(O)(OR^{11})$ and $P(O)(R^{11})$; substituted or unsubstituted aryl; substituted or unsubstituted heteroaryl, or substituted or unsubstituted 2,2,7,7-tetramethyl isoindolinoxyl, substituted or unsubstituted 2,2,7,7-tetraethyl isoindolinoxyl; or
- $R^3$ and $R^4$ are joined, through the double bond C=$X_3$ to form together with the nitrogen atom to which they are bound a 5- to 8-membered heterocyclic ring and which may contain an additional heteroatom or heteroatomic group selected from $P(O)(OR^{11})$, $P(O)(R^{11})$, O, S, $N^+$—$O^-$, NH, $N(C_1-C_6$ alkyl) wherein the alkyl is straight, branched or cyclic, wherein the heterocyclic ring bears from one substituent to the maximum number of substituent on the carbon atoms and optionally contains one double bond; and with the proviso that the two groups $R^3$ or $R^4$ together do not contain more than one hydrogen alpha to the (N—O.) group;
  with the proviso that a compound of formula

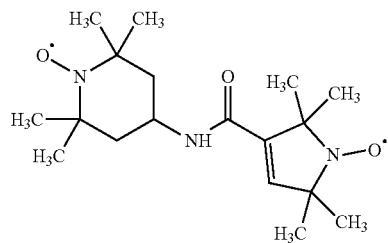

is excluded.

By this invention, the inventors have designed a new family of powerful polarizing agents with high magnetic field and high frequency MAS. This new generation of molecules, based on symmetrical or asymmetric dinitroxides, uses in particular a new type of chemical bridge.

The chemical bridge or linkage presented in the compounds of formula (I) is a conjugate bridge that provides stiffness and rigidity which reduces the distance between the nitroxide units and promotes the efficient transfer of polarization. It is worth noting that the optimal polarizing agent structure is a complex multi-parameter problem which implies for instance, the distance between the two nitroxides, the intensity of the J-exchange interaction, the relative orientation between the two nitroxides, as well as the associated electronic relaxation times and deuteration level of the polarizing agent.

The design of these new compounds did not consist solely in trying to maximize the $\varepsilon_{on/off}$ amplification factor but also to minimize depolarization effects while maximizing the effectiveness of the transfer of polarization. The inventors aimed at maximizing the sensitivity under DNP conditions, defined by $\varepsilon_B/\sqrt{T_B}$, where $\varepsilon_B$ and $T_B$ represent the real enhancement factor corrected from depolarization effect and the polarization buildup time respectively. (F. Mentink-Vigier, S. Paul, D. Lee, A. Feintuch, S. Hediger, S. Vega and G. De Paëpe, *Phys. Chem. Chem. Phys.,* 2015, 17, 21824. and F. Mentink-Vigier, S. Vega and G. De Paëpe, *Phys. Chem. Chem. Phys.,* 2017, 19, 3506-3522.)

With the goal to increase the interaction between unpaired electrons (called dipolar coupling and/or J exchange interaction) and constrain the relative orientation of the two paramagnetic centers (e.g. the planes of the TEMPO groups), the inventors found that a conjugated chemical bridge as in compounds of formula (I), reduces the number of atoms involved in the bridge. Such conjugated bridge brings the two electron spins closer while maintaining a suitable relative orientation between the two nitroxide groups (N—O.) (or their corresponding g-tensors) to perform CE DNP.

Due to the strong interaction between the resulting electronic spins and their relative orientation, the polarization transfer efficiency defined by $\varepsilon_B$ (and not the amplification factor $\varepsilon_{on/off}$) can be maximized and the polarization rise time $T_B$ can be minimized.

The term "$C_{1-6}$ aliphatic group", as used herein, includes both saturated and unsaturated, non aromatic, straight chain (i.e. unbranched), branched, acyclic and cyclic (i.e. carbocyclic) hydrocarbons having 1-6 carbon atoms, which are optionally substituted with one or more functional groups. The term "aliphatic", as used herein, includes $C_{1-6}$ alkyl, $C_{2-6}$ alkenyl, $C_{2-6}$ alkynyl, $C_{3-7}$ cycloalkyl, $C_{3-7}$ cycloalkenyl and $C_{5-7}$ cycloalkynyl moieties. Thus, as used herein, the term "$C_{1-6}$ alkyl" includes straight, branched and cyclic hydrocarbons having 1-6 carbon atoms. Similarly, the terms "$C_{2-6}$ alkenyl" and "$C_{2-6}$ alkynyl", includes straight, branched, unsaturated and cyclic hydrocarbons having 2-6 carbon atoms and at least one unsaturation (a double and/or triple bond).

Substituents in a substituted $C_{1-6}$ aliphatic group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $-NR^{10}_2$; $=NR^{10}$; $-COOH$; $COOR^{10}$; $-CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. The number of substituents present in a substituted $C_{1-6}$ aliphatic group may be up to the number of the hydrogen atoms available for a substitution, but is preferably 1-2, more preferably 1.

The term "$C_{1-6}$ alkyl" as used herein, refers to saturated, straight- or branched-chain or cyclic hydrocarbon radicals derived from a hydrocarbon moiety containing from 1 to 6 carbon atoms by removal of a single hydrogen atom. Examples of $C_{1-6}$ alkyl radicals include methyl, ethyl, n-propyl, isopropyl, n-butyl, iso-butyl, sec-butyl, sec-pentyl, isopentyl, tert-butyl, n-pentyl, neopentyl, n-hexyl, sec-hexyl, cyclopropyl, cyclopropylmethyl, cyclopentyl and cyclohexyl. The term "$C_{1-4}$ alkyl", as used herein, refers to saturated, straight- or branched-chain hydrocarbon radicals derived from a hydrocarbon moiety containing from 1 to 4 carbon atoms by removal of a single hydrogen atom. Examples of $C_{1-4}$ alkyl radicals include methyl, ethyl, n-propyl, isopropyl, n-butyl, iso-butyl, sec-butyl. The term "$C_{1-18}$ alkyl" as used herein, refers to saturated, straight- or branched-chain hydrocarbon radicals derived from a hydrocarbon moiety containing from 1 to 18 carbon atoms by removal of a single hydrogen atom.

The term "$C_{3-7}$ cycloalkyl" refers to cyclic hydrocarbon radicals derived from a hydrocarbon moiety containing from 3 to 7 carbon atoms by removal of a single hydrogen atom. Examples of $C_{3-7}$ cycloalkyl include cyclopropyl, cyclopropylmethyl, cyclobutyl, cyclobutylmethyl, cyclopentyl, cyclopentylmethyl, cyclohexyl, and cyclohexylmethyl.

The above-mentioned alkyl or cycloalkyl groups may bear one or more substituents. Substituents in a substituted $C_{1-6}$ alkyl, $C_{1-4}$ alkyl or $C_{3-7}$ cycloalkyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $-NR^{10}_2$; $=NR^{10}$; $-COOH$; $COOR^{10}$; $-CONR^{10}2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. The number of substituents present in a substituted $C_{1-6}$ alkyl group may be up to the number of the hydrogen atoms available for a substitution, but is preferably 1-2, more preferably 1.

The term "$C_{2-6}$ alkenyl", as used herein, refers to a monovalent group derived from a straight- or branched-chain or cyclic hydrocarbon moiety having at least one carbon-carbon double bond. The $C_{2-6}$ alkenyl contains 2 to 6 carbon atoms. $C_{2-6}$ alkenyl groups include, for example, ethenyl, propenyl, isopropenyl, 1- or 2-butenyl, 1-methyl-2-buten-1-yl and cyclopentenyl. $C_{2-4}$ alkenyl, as used herein, refers to a monovalent group derived from a straight- or branched-chain or cyclic hydrocarbon moiety having at least one carbon-carbon double bond. The $C_{2-4}$ alkenyl contains 2 to 4 carbon atoms. $C_{2-4}$ alkenyl groups include, for example, ethenyl, propenyl, isopropenyl, 1- or 2-butenyl.

The above-mentioned $C_{2-6}$ or $C_{2-4}$ alkenyl groups may bear one or more substituents. Substituents in a substituted $C_{2-6}$ or $C_{2-4}$ alkenyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $-NR^{10}_2$; $=NR^{10}$; $-COOH$; $COOR^{10}$; $-CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. The number of substituents present in a substituted $C_{2-6}$ or $C_{2-4}$ alkenyl group may be up to the number of the hydrogen atoms available for a substitution, but is preferably 1-2, more preferably 1.

The term "$C_{2-6}$ alkynyl", as used herein, refers to a monovalent group derived from a straight- or branched-chain or cyclic hydrocarbon moiety having at least one carbon-carbon triple bond. The $C_{2-6}$ alkynyl contains 2 to 6 carbon atoms. $C_{2-6}$ alkynyl groups include, for example, ethynyl, 2-propynyl (propargyl), 1-propynyl and cyclohexynyl. $C_{2-4}$ alkynyl, as used herein, refers to a monovalent group derived from a straight- or branched-chain or cyclic hydrocarbon moiety having at least one carbon-carbon triple bond. The $C_{2-4}$ alkynyl groups contain 2 to 4 carbon atoms. $C_{2-4}$ alkynyl groups include, for example, ethynyl, 2-propynyl (propargyl), 1-propynyl.

The above-mentioned $C_{2-6}$ or $C_{2-4}$ alkynyl groups may bear one or more substituents. Substituents in a substituted $C_{2-6}$ or $C_{2-4}$ alkynyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $-NR^{10}_2$, $=NR^{10}$, $-COOH$, $COOR^{10}$, $-CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. The number of substituents present in a substituted $C_{2-6}$ or $C_{2-4}$ alkynyl group may be up to the number of the hydrogen atoms available for a substitution, but is preferably 1-2, more preferably 1.

The term "$C_{1-6}$ heteroaliphatic group", as used herein, includes both saturated and unsaturated, non aromatic, straight chain (i.e. unbranched), branched, acyclic and cyclic (i.e. heterocyclic) hydrocarbons, which are optionally substituted with one or more functional groups and that contain one oxygen, sulfur, substituted nitrogen or substituted phosphorous atom in place of one carbon atom. A heteroaliphatic group according to the invention has 1-5 carbon atoms. The term "$C_{1-6}$ heteroaliphatic group" includes heteroalkyl, heteroalkenyl, heteroalkynyl and heterocyclyl moieties. Thus, as used herein, the term "heteroalkyl" includes straight, branched and cyclic alkyl groups as defined herein, which are substituted with one or more functional groups, and that contain one oxygen, sulfur, nitrogen or phosphorous atom in place of one carbon atom. An analogous convention applies to other generic terms such as "heteroalkenyl" and "heteroalkynyl". The substituent of the nitrogen atom is the substituent $R^a$, as defined in the context of the present invention. Phosphorous is present as P(O)OH, P(O)($C_{1-18}$ alkoxy) or P(O)($C_{1-18}$ alkyl). The term "substituted $C_{1-6}$ heteroaliphatic group" denotes that one or more carbon atoms may also bear a substituent.

Substituents on carbon atoms of the $C_{1-6}$ heteroaliphatic group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $—NR^{10}_2$, $=NR^{10}$, $—COOH$, $COOR^{10}$, $—CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. The number of substituents present in a substituted $C_{2-6}$ or $C_{2-4}$ alkynyl group may be up to the number of the hydrogen atoms available for a substitution, but is preferably 1-2, more preferably 1.

The term "aryl", as used herein, refers to stable mono- or bicyclic ring system having 5-10 ring atoms, of which all the ring atoms are carbon, and which may be substituted or unsubstituted. Aryl includes, for example, phenyl, biphenyl and naphtyl, which may bear one or more substituents;

Aryl substituents include $C_{1-6}$ alkyl, $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $—NR^{10}_2$; $=NR^{10}$; $—COOH$; $COOR^{10}$; $—CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl.

2,2,7,7-Tetramethyl isoindolinoxyl and 2,2,7,7-tetraethyl isoindolinoxyl substituents on the benzene ring are the same as the aryl substituents.

Preferably aryl is unsubstituent phenyl or phenyl substituted with one of the above substituents.

The term "heteroaryl", as used herein, refers to stable mono- or bicyclic ring system having 5-12 ring atoms, of which one ring atom is selected from S, O, and N and the remaining atoms are carbon. 0, 1 or 2 ring atoms are additional heteroatoms independently selected from S, O and N and the remaining atoms are carbon. The heteroaryl radical may be joined to the rest of the molecule via any of the ring atoms.

Exemplary heteroaryls include pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolynyl, phtalazinyl, naphthridinyl, quinoxalinyl, thiophenyl, thianaphthznyl, furanyl, benzofuranyl, benzothiazolyl, thiazolynyl, isothiazolyl, thiadiazolynyl, oxazolyl, isoxazolyl, oxadiazolyl and oxadiazolyl may bear one or more substituents. Heteroaryl substituents include $C_{1-6}$ alkyl, $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $—NR^{10}_2$; $=NR^{10}$; $—COOH$; $COOR^{10}$; $—CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl.

Preferably heteroaryl is pyrrol, pyrazolyl, imidazolyl, pyridinyl, pyrimidinyl, pyrazinyl, pyridazinyl, furanyl and thiophenyl, each substituted or unsubstituted with one of the above substituents.

The term "heterocyclic ring", as used herein, refers to a non aromatic, partially unsaturated or fully saturated, 5- to 8-membered ring. These heterocyclic rings include those having 1 to 3 heteroatoms independently selected from oxygen, sulfur, phosphorous and nitrogen, in which the nitrogen, phosphorous and sulfur heteroatoms may optionally be oxidized and the nitrogen heteroatom may optionally be quaternized. In certain embodiments, the term heterocyclic ring refers to a non aromatic 5-, 6-, 7- or 8-membered ring wherein at least one ring atom is a heteroatom selected from oxygen, sulfur, phosphorous and nitrogen wherein the substituent of the nitrogen atom is $R^{10}$ as defined above, and phosphorous is present as P(O)OH, P(O)$OR^{11}$ or P(O)$R^{11}$, with $R^{11}$ being a linear or branched $C_{1-18}$ alkyl. The remaining atoms of the heterocyclic ring are carbon atoms, and said ring is joined to the rest of the molecule via any of the carbon ring atoms.

Substituents on carbon atoms of the heterocyclic rings include $C_{1-6}$ alkyl, $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen; hydroxyl; thiol; nitro; cyano; $—NR^{10}_2$; $=NR^{10}$; $—COOH$; $COOR^{10}$; $—CONR^{10}_2$ and $SO_2NR^{10}_2$, wherein $R^{10}$ is independently hydrogen, hydroxyl, substituted or unsubstituted linear, branched or cyclic $C_{1-6}$ alkyl, $C_{1-6}$ alkylcarbonyl, substituted or unsubstituted aryl sulfinyl, or substituted or unsubstituted aryl sulfonyl. Furthermore, any two geminal substituents of heterocyclic rings may be joined to form together with the secondary carbon atom to which they are bound a cyclopentane or cyclohexane ring which may be further substituted with one or more substituents as defined above for alkyl groups, or a 5- or 6-membered heterocyclic ring comprising one atom or group selected from O, S, $NR^{10}$ with $R^{10}$ as previously defined, P(O)OH, P(O)($C_{1-6}$ alkyl) and P(O)(O$C_{1-6}$ alkyl) which may be further substituted on one or more carbon atoms with a substituent as defined above in this paragraph.

The term "hydroxy" or "hydroxyl", as used herein, refers to —OH.

The term "$C_{1-4}$ alkoxy" refers to a group of formula —$OR^a$ wherein $R^a$ is $C_{1-4}$ alkyl. The term "$C_{1-18}$ alkoxy" refers to a group of formula —$OR^b$ wherein $R^b$ is $C_{1-18}$ alkyl.

The term "$C_{1-4}$ hydroxyalkyl" refers to a $C_{1-4}$ alkyl group bearing one hydroxyl in place of any hydrogen atom.

The term "cyano", as used herein, refers to —CN.

The term "direct bond" or "bond" refers to a single, double or triple bond between two groups. In certain embodiments, a direct bond refers to a single bond between two groups.

The terms "halo" and "halogen", as used herein, refer to an atom selected from fluorine (fluoro —F), chlorine (chloro —Cl), bromine (bromo —Br), and (iodine (iodo —I).

The term "nitro", as used herein, refers to —NO$_2$.

The term "nitroxide", as used herein, refers to a stable cyclic or acyclic compound comprising at least one aminoxyl group. In certain embodiments, a stable nitroxide refers to a chemically stable nitroxide which may be obtained in pure form, stored and handled in the laboratory. In certain embodiments, a stable nitroxide refers to a cyclic or acyclic nitroxide which contains two groups which do not contain alpha hydrogens. Exemplary cyclic or acyclic nitroxides are provided, for example, in J. F. W. Keana, Chemical Reviews, 1978, 78, pp. 37-64.

A "dinitroxide biradical" or a "dinitroxide compound", as used herein, refers to a stable cyclic or acyclic compound comprising two aminoxyl groups in two separate nitroxide containing moieties.

The term "$C_{1-4}$ alkylsulfinyl" and "$C_{1-6}$ alkylsulfinyl", as used herein, refers to a group of formula $C_{1-4}$ alkyl-S(=O)— and $C_{1-6}$ alkyl-S(=O)—, respectively.

The term "aryl sulfinyl", as used herein, refers to aryl-S(=O)—.

The term "$C_{1-4}$ alkyl sulfonyl" and "$C_{1-6}$ alkyl sulfonyl", as used herein, refers to a group of formula $C_{1-4}$ alkyl-S(=O)$_2$— and $C_{1-6}$ alkyl-S(=O)$_2$—, respectively.

The term "aryl sulfonyl", as used herein, refers to aryl-S(=O)$_2$—.

In a first embodiment of the invention, in the compounds of formula (I), $Q_1$ is a cyclic nitroxide radical, as represented below

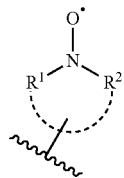

wherein $R^1$ and $R^2$ are joined, as indicated by ⌣ to form together with the nitrogen atom to which they are bound a 5- to 8-membered heterocyclic ring and which may contain an additional heteroatom or heteroatomic group selected from P(O)(OR$^{11}$), P(O)(R$^{11}$), O, S, N$^+$—O$^-$, NH, N(C$_{1}$-C$_6$ alkyl) wherein the alkyl is straight, branched or cyclic, wherein the heterocyclic ring bears from one substituent to the maximum number of substituent on the carbon atoms and optionally contains one double bond; and with the proviso that the two groups $R^1$ or $R^2$ together do not contain more than one hydrogen alpha to the (N—O.) group; and $R^{11}$ is linear or branched C$_{1-18}$ alkyl, H or an alkali metal.

In this first embodiment, X$_1$, X$_2$, X$_3$, R$^3$-R$^{10}$, m, n, p and q are as described above.

In this first embodiment, $Q_1$ is a nitroxide-containing a 5- to 8-membered heterocyclic ring, substituted at least at all positions alpha to the (N—O.) group, selected from

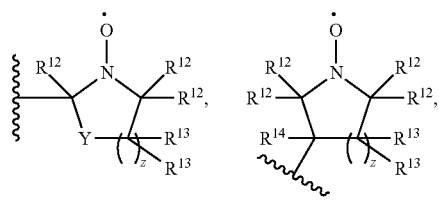

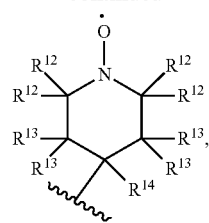

wherein z is 1 or 2;

Y is selected from —O—, —S—, —NR with R being hydrogen, substituted or unsubstituted linear, branched or cyclic C$_{1-6}$ alkyl, or —CHR— with R being hydrogen, substituted or unsubstituted linear, branched or cyclic C$_{1-6}$ alkyl; =C R$^{13}$ and R$^{14}$ are, independently, hydrogen, hydroxyl, substituted or unsubstituted linear, branched or cyclic C$_{1-6}$ alkyl;

R$^{12}$ is, independently, hydrogen, hydroxyl, substituted or unsubstituted linear, branched or cyclic C$_{1-6}$ alkyl, or two geminal R$^{12}$ are joined to form together with the secondary carbon to which they are bound a substituted or unsubstituted cyclopentane, cyclohexane, a 5- or 6-membered heterocyclic ring wherein at least one ring atom is oxygen.

In this first embodiment, $Q_1$ is, preferably,

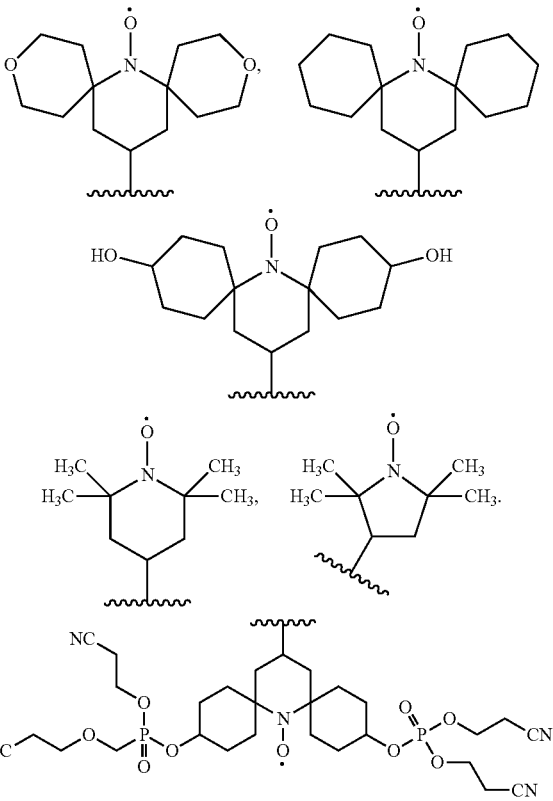

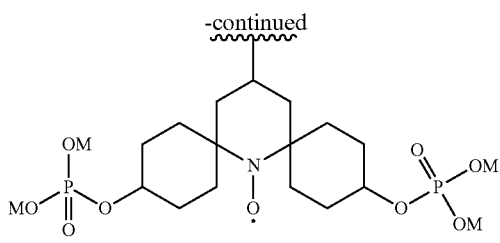

wherein M is an alkali metal selected in the group consisting of lithium (Li), sodium (Na), potassium (K), rubidium (Rb) and cesium (Cs). Preferably, M is lithium (Li), sodium (Na) and potassium (K).

In a second embodiment of the invention, in the compounds of formula (I), $Q_1$ is an acyclic nitroxide radical, as represented below

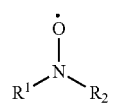

wherein $R^1$ and $R^2$ are, independently, a substituted or unsubstituted, linear, branched or cyclic $C_{1-6}$ aliphatic group; a substituted or unsubstituted linear, branched or cyclic hetero-aliphatic group comprising 5 carbon atoms and one heteroatom or heteroatomic group, respectively, selected from O, S, —$NR^{10}$—, $P(O)(OR^{11})$ and $P(O)(R^{11})$; substituted or unsubstituted aryl; substituted or unsubstituted heteroaryl, or substituted or unsubstituted 2,2,7,7-tetramethyl isoindolinoxyl; or substituted or unsubstituted 2,2,7,7-tetraethyl isoindolinoxyl;

with the proviso that the two groups $R^1$ or $R^2$ together do not contain more than one hydrogen alpha to the (N—O.) group.

In this second embodiment, $X_1$, $X_2$, $X_3$, $R^3$-$R^{11}$, m, n, p and q are as described above.

In this second embodiment, $Q_1$ may be an acyclic nitroxide radical wherein $R^1$ and $R^2$ can be aliphatic, heteroaliphatic, aromatic, heteroaromatic groups wherein "aliphatic" is a substituted or unsubstituted linear, branched or cyclic $C_1$-$C_6$ aliphatic group; and "heteroaliphatic" is a substituted or unsubstituted linear, branched or cyclic group heteroaliphatic group comprising 5 C atoms and one heteroatom or heterogroup, respectively, selected from O, S, N($R^{12}$), P($R^{12}$), P(=O)OH and P(=O)O($C_{1-6}$ alkyl); "aromatic" and "heteroaromatic" are substituted or unsubstituted "aryl" and "heteroaryl" respectively, as defined above; with the proviso that the two groups, which are selected from heteroaliphatic, aromatic or heteroaromatic group and are attached to the nitrogen atom of the (N—O.) group, together do not contain more than one hydrogen alpha to the (N—O.) group; and a nitroxide-containing 5- to 8-membered heterocyclic ring, which may contain an additional heteroatom or heteroatomic group selected from O, S, $N^+$—$O^-$, NH, N($C_{1-16}$ alkyl) wherein the alkyl is straight, branched or cyclic, and may contain one double bond and is substituted at least at all positions alpha to the (N—O.) group, the substituents being selected from those mentioned above in the context of the definition of "heterocyclic group".

In this second embodiment, $Q_1$ is, preferably,

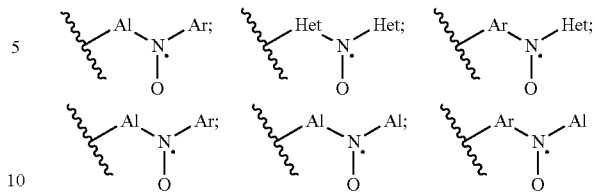

wherein
"Ar" is substituted or unsubstituted aryl; "Al" is a substituted or unsubstituted linear, branched or cyclic $C_1$-$C_6$ aliphatic group; and "Het" is a substituted or unsubstituted heteroaryl as defined herein.

Examples of $Q_1$ in this second embodiment are:

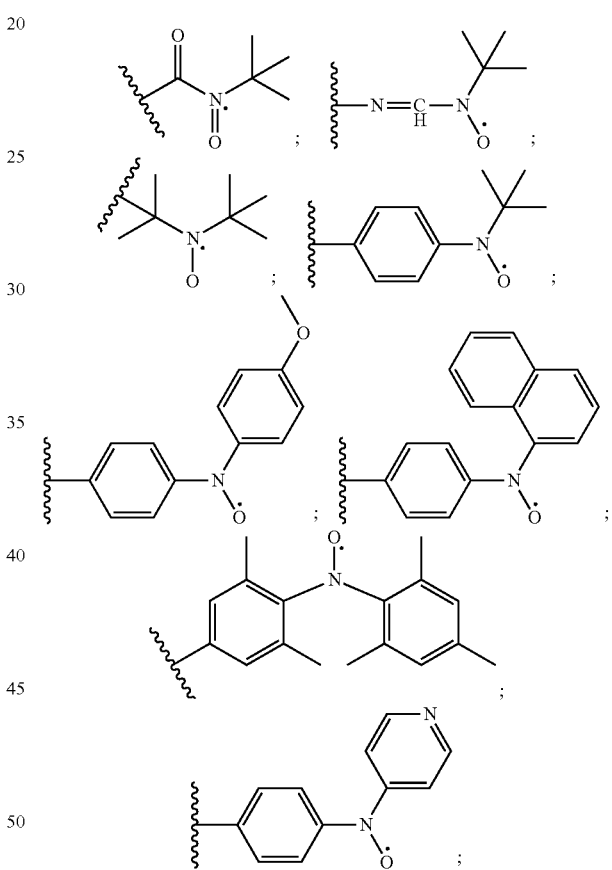

In a third embodiment of the invention, $R^3$ and $R^4$ are joined, through the double bond C=$X_3$ to form together with the nitrogen atom to which they are bound a 5- to 8-membered heterocyclic ring and which may contain an additional heteroatom or heteroatomic group selected from $P(O)(OR^{11})$, $P(O)(R^{11})$, O, S, $N^+$—$O^-$, NH, N($C_1$-$C_6$ alkyl) wherein the alkyl is straight, branched or cyclic, wherein the heterocyclic ring bears from one substituent to the maximum number of substituent on the carbon atoms and optionally contains one double bond; and
with the proviso that the two groups $R^3$ or $R^4$ together do not contain more than one hydrogen alpha to the (N—O.) group.

In this third embodiment, $X_1$, $X_2$, $X_3$, $R^5$-$R^{10}$, m, n, p and q are as described above.

In this third embodiment, $R^3$ and $R^4$ are joined, through the double bond $C=X_3$ to form together with the nitrogen atom to which they are bound a 5- to 8-membered heterocyclic ring, as represented below

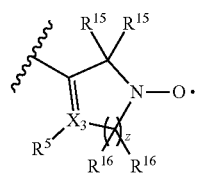

wherein z is 1 or 2;

$X_3$ is C or N with the proviso that when $X_3$ is N, then $R^5$ is not present in the molecule;

$R^5$ is H; $(CH_2)_n$—COOH with n being an integer from 1 to 10, —OH, —NH$_2$, —$(CH_2—CH_2—O)_m$—CH$_3$ or $(CH_2—CH_2—O)_m$—H with m being an integer from 1 to 10;

$R^{15}$ and $R^{16}$ are, independently, hydroxyl, substituted or unsubstituted linear, branched or cyclic $C_{1-6}$ alkyl; or two geminal $R^{15}$ or $R^{16}$ are joined to form together with the secondary carbon to which they are bound a substituted or unsubstituted cyclopentane, cyclohexane, a 5- or 6-membered heterocyclic ring wherein at least one ring atom is oxygen.

In this third embodiment, preferably $R^3$ and $R^4$ are joined and form together with the nitrogen atom to which they are bound a 5-membered heterocyclic ring selected from

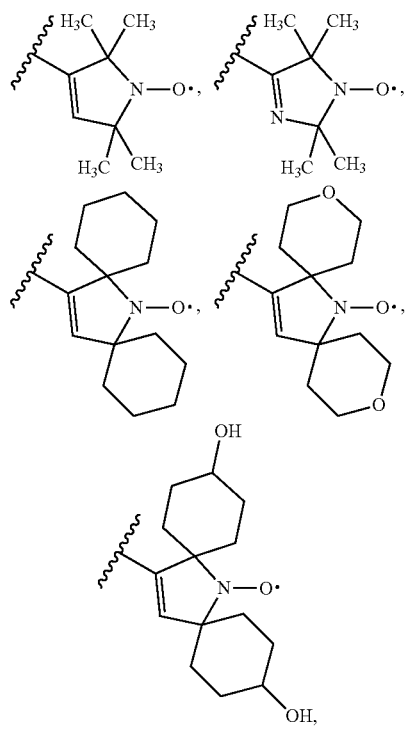

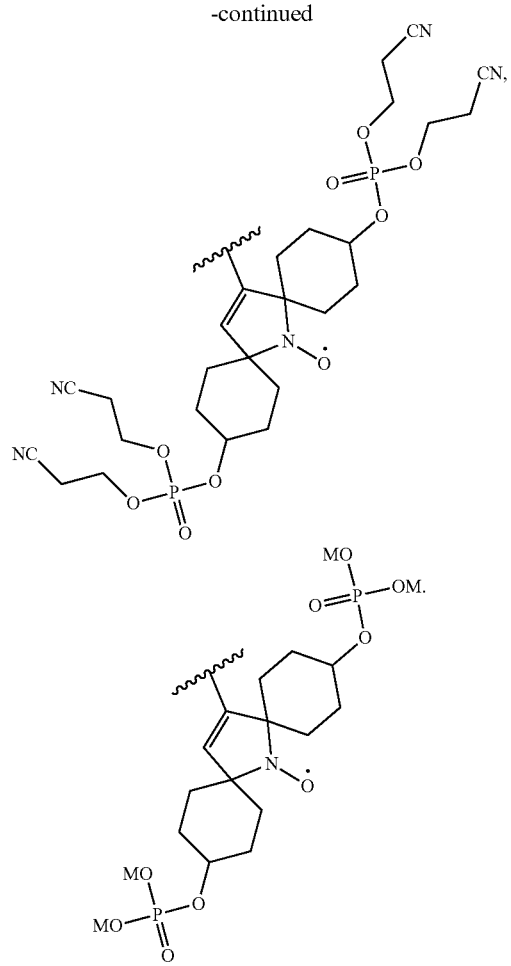

wherein M is an alkali metal selected in the group consisting of lithium (Li), sodium (Na), potassium (K), rubidium (Rb) and cesium (Cs). Preferably, M is lithium (Li), sodium (Na) and potassium (K).

In a fourth embodiment of the invention, in the compounds of formula (I), $Q_1$ is a cyclic nitroxide radical, as represented below

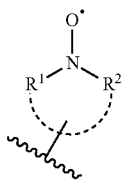

wherein $R^1$ and $R^2$ are joined, as indicated by ⌣ to form together with the nitrogen atom to which they are bound a 5- to 8-membered heterocyclic ring and which may contain an additional heteroatom or heteroatomic group selected from $P(O)(OR^{11})$, $P(O)(R^{11})$, O, S, $N^+$—O$^-$, NH, N(C$_1$-C$_6$ alkyl) wherein the alkyl is straight, branched or cyclic, wherein the heterocyclic ring bears from one substituent to the maximum number of substituent on the carbon atoms and optionally contains one double bond; and with the proviso that the two groups $R^1$ or $R^2$ together do not contain more than one hydrogen alpha to the (N—O.) group;

$R^1$ is linear or branched $C_{1-18}$ alkyl, H or an alkali metal;

$X_3$ is C or N with the proviso that when $X_3$ is N, then $R^5$ is not present in the molecule;

$R^3$ and $R^4$ are joined, through the double bond C=$X_3$ to form together with the nitrogen atom to which they are bound a 5- to 8-membered heterocyclic ring and which may contain an additional heteroatom or heteroatomic group selected from $P(O)(OR^{11})$, $P(O)(R^{11})$, O, S, $N^+$—$O^-$, NH, N($C_1$-$C_6$ alkyl) wherein the alkyl is straight, branched or cyclic, wherein the heterocyclic ring bears from one substituent to the maximum number of substituent on the carbon atoms and optionally contains one double bond; and with the proviso that the two groups $R^3$ or $R^4$ together do not contain more than one hydrogen alpha to the (N—O.) group.

In this fourth embodiment, $X_1$, $X_2$, $R^5$-$R^{10}$, m, n, p and q are as described above.

In this fourth embodiment, $Q_1$ is a nitroxide-containing a 5- to 8-membered heterocyclic ring, substituted at least at all positions alpha to the (N—O.) group, selected from

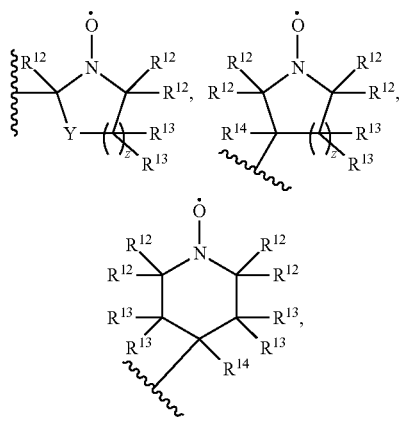

wherein z is 1 or 2;

Y is selected from —O—, —S—, —NR with R being hydrogen, substituted or unsubstituted linear, branched or cyclic $C_{1-6}$ alkyl, or —CHR— with R being hydrogen, substituted or unsubstituted linear, branched or cyclic $C_{1-6}$ alkyl;

$R^{13}$ and $R^{14}$ are, independently, hydrogen, hydroxyl, substituted or unsubstituted linear, branched or cyclic $C_{1-6}$ alkyl;

$R^{12}$ is, independently, hydrogen, hydroxyl, substituted or unsubstituted linear, branched or cyclic $C_{1-6}$ alkyl, or two geminal $R^{12}$ are joined to form together with the secondary carbon to which they are bound a substituted or unsubstituted cyclopentane, cyclohexane, a 5- or 6-membered heterocyclic ring wherein at least one ring atom is oxygen;

$R^3$ and $R^4$ are joined, through the double bond C=$X_3$ to form together with the nitrogen atom to which they are bound a 5- to 8-membered heterocyclic ring, as represented below

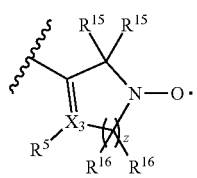

wherein z is 1 or 2;

$X_3$ is C or N with the proviso that when $X_3$ is N, then $R^5$ is not present in the molecule;

$R^5$ is H; $(CH_2)_n$—COOH with n being an integer from 1 to 10, —OH, —$NH_2$, —$(CH_2$—$CH_2$—$O)_m$—$CH_3$ or $(CH_2$—$CH_2$—$O)_m$—H with m being an integer from 1 to 10;

$R^{15}$ and $R^{16}$ are, independently, hydroxyl, substituted or unsubstituted linear, branched or cyclic $C_{1-6}$ alkyl; or two geminal $R^{15}$ or $R^{16}$ are joined to form together with the secondary carbon to which they are bound a substituted or unsubstituted cyclopentane, cyclohexane, a 5- or 6-membered heterocyclic ring wherein at least one ring atom is oxygen.

In this fourth embodiment, preferably, $Q_1$ is

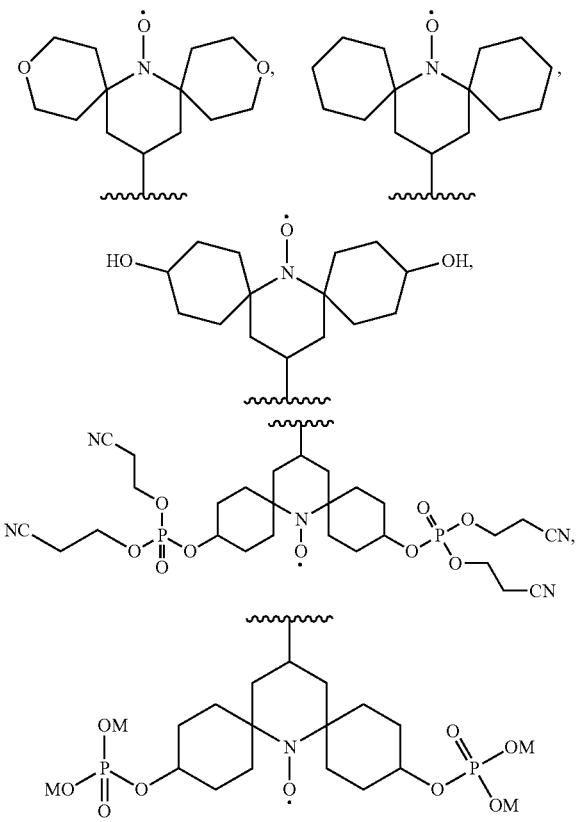

with M being an alkali metal selected in the group consisting of lithium (Li), sodium (Na), potassium (K), rubidium (Rb) and cesium (Cs). Preferably, M is lithium (Li), sodium (Na) and potassium (K),

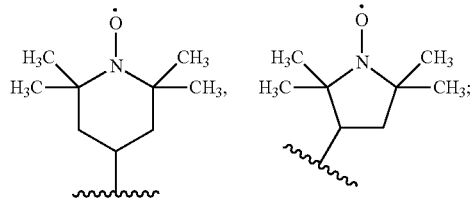

$R^3$ and $R^4$ are joined and form together with the nitrogen atom to which they are bound a 5-membered heterocyclic ring selected from

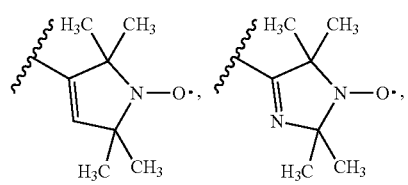

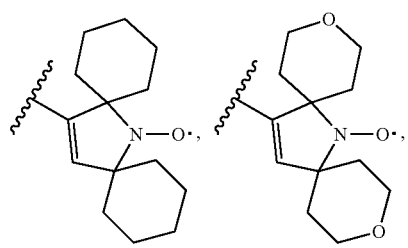

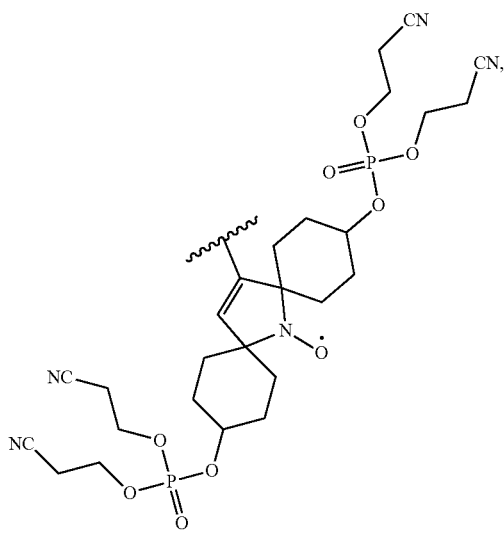

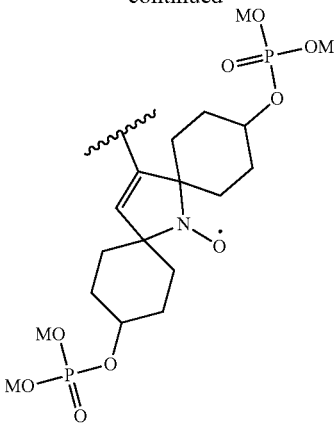

with M being an alkali metal selected in the group consisting of lithium (Li), sodium (Na), potassium (K), rubidium (Rb) and cesium (Cs). Preferably, M is lithium (Li), sodium (Na) and potassium (K), In all the embodiments disclosed herein, $X_1$ is preferably O.

In all the embodiments disclosed herein, $X_2$ is preferably O or —$NR^9$ wherein $R^9$ is H; a substituted or unsubstituted, linear, branched or cyclic $C_{1-6}$ aliphatic group; —$(CH_2)_n$—COOH with n being an integer from 1 to 10, —$(CH_2$—$CH_2$—$O)_m$—$CH_3$ or —$(CH_2$—$CH_2$—$O)_m$—H with m being an integer from 1 to 500, preferably from 1 to 100, more preferably from 1 to 10.

In all the embodiments disclosed herein, $X_2$ is preferably O.

In all the embodiments disclosed herein, $X_2$ is more preferably —$NR^9$ wherein $R^9$ is H; a substituted or unsubstituted, linear, branched or cyclic $C_{1-6}$ aliphatic group; —$(CH_2$—$CH_2$—$O)_m$—$CH_3$ or —$(CH_2$—$CH_2$—$O)_m$—H with m being an integer from 1 to 10.

In all the embodiments disclosed herein, $X_2$ is still more preferably —$NR^9$ wherein $R^9$ is H, a linear or branched $C_{1-6}$ alkyl, —$(CH_2$—$CH_2$—$O)_m$—$CH_3$ with m being 1 to 10.

In a fifth embodiment of the invention, the compound of formula (I) is

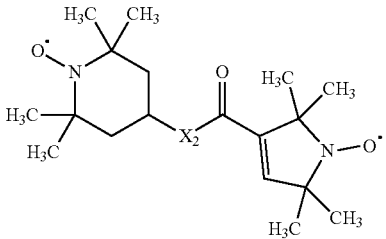

with $X_2$ as defined above;

with the proviso that the compound of formula

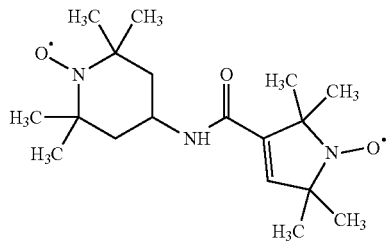

is excluded.

The presence of "small" cycles in the compounds of formula (I) creates strong interactions between electronic spins.

Compound 3 (referred to as AsymPol)

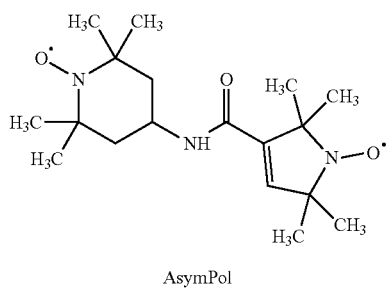

AsymPol described herein is excluded from the definition of the compounds of formula (I). In an exemplary embodiment according to the invention, the compound of formula (I) is compound 7:

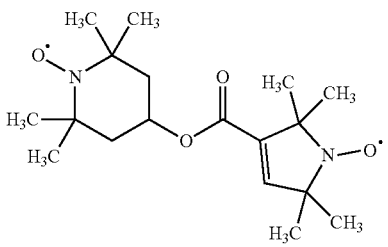

7

In an exemplary embodiment according to the invention, the compound of formula (I) is compound 5:

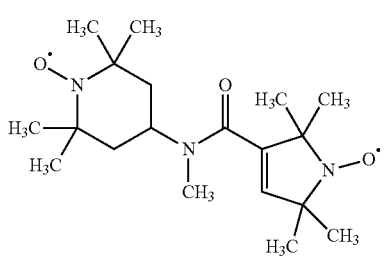

5

In an exemplary embodiment according to the invention, the compound of formula (I) is compound 10 (referred to as AsymPol II):

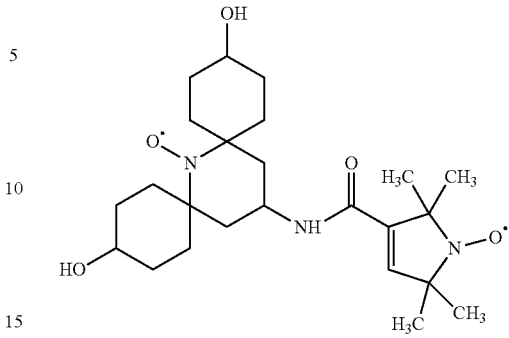

AsymPol II

In an exemplary embodiment according to the invention, the compound of formula (I) is compound 13:

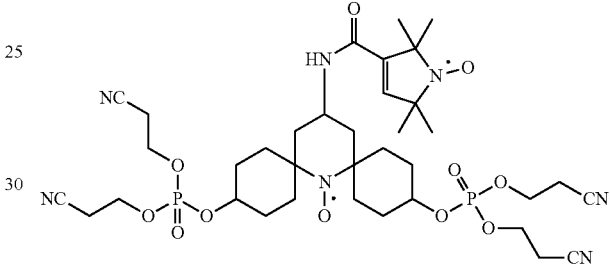

13

In an exemplary embodiment according to the invention, the compound of formula (I) is compound 14: (referred to as AsymPolPOK):

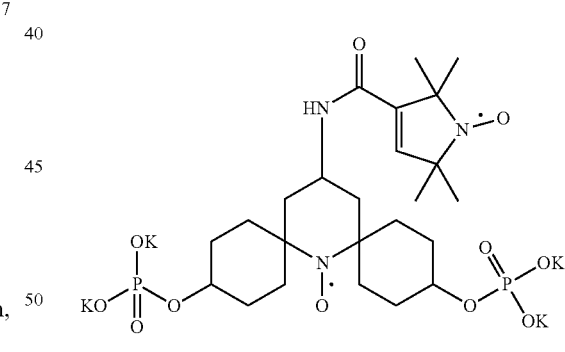

AsymPolPOK

Syntheses of particular compounds of formula (I) according to the invention are described in details in the Examples.

In a general manner, syntheses of these biradicals were done by coupling of respective carboxy and amino components using peptide coupling agents that are commonly used during peptide synthesis (A. El-Faham and F. Albericio, Chem. Rev., 2011, 111, 6557-6602). Here, we used dicyclohexyl carbodiimide (DCC) and 1-hydroxybenzotriazole (HOBt) as a coupling agents for the preparation of biradicals.

A general method for the synthesis of the AsymPol family of biradicals is given below.

The compounds of the invention can be obtained according to a one-step synthesis as shown below:

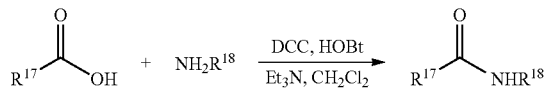

wherein $R^{17}$ and $R^{18}$ are cyclic or acyclic nitroxides as defined above. The carboxy component ($R^{17}$—COOH) and amino component ($NH_2R^{18}$) are the starting materials, and DCC/HOBt are reagents.

The carboxy component ($R^{17}$—COOH) can be either activated in-situ or by using its more reactive derivatives, such as acyl halides, acyl azides, acylimidazoles, anhydrides or esters. Reaction of an activated form of the carboxy component with the amino component ($NH_2R^{18}$) will form an amide as the desired coupling product.

For in-situ activation of the carboxy component ($R^{17}$—COOH), coupling agents that are commonly used for peptide synthesis can be used, such as carbonyl diimidazole (CDI), N,N'-carbonylbis(3-methylimidazolium) triflate (CBMIT), diisopropyl carbodiimide (DIC), dicyclohexyl carbodiimide (DCC), 1-ethyl-3-(3'-dimethylamino)carbodiimide.HCl (EDCI), benzotriazol-1-yl-oxy oxytris-(dimethylamino)-phosphonium hexafluorophosphate (BOP), benzotriazol-1-yl-oxy-tris-pyrrolidinophosphonium hexafluorophosphate (PyBop) and phosphonium-based coupling reagents, with or without hydroxybenzotriazole (HOBt) or hydroxy-7-azabenzotriazole (HOAt) as a co-reagent. More preferably DCC/HoBt was used as a coupling agent for the biradical synthesis.

The solvents used for the reaction may be the same or selected from diethylether, dimethylether, dioxane, dichloromethane, dichloroethane, acetonitrile, chloroform, dimethylformamide (DMF), dimethylsulfoxide (DMSO), tetrahydrofurane (THF) or toluene.

A tertiary amine that was used during the reaction can be triethyl amine ($Et_3N$), N,N-diisopropylethylamine (Hünig's base or DIPEA) or 4-dimethylaminopyridine (DMAP); more preferably triethyl amine.

The reaction temperature can be between 20 and 50° C., preferably between 20 and 30° C.

The reaction time can be between 1 and 48 h, more preferably between 6 and 24 h.

The molar ratio between carboxy component ($R^{17}$—COOH) and amino component ($NH_2R^{18}$) can be between 1 and 1.5, in particular between 1 and 1.2.

The molar ratio between carboxy component ($R^{17}$—COOH) and the reagent DCC can be between 1 and 1.5, in particular between 1 and 1.2.

The molar ratio between carboxy component ($R^{17}$—COOH) and the reagent HOBt can be between 1 and 5, in particular between 2 and 3.

The molar ratio between carboxy component ($R^{17}$—COOH) and the $Et_3N$ can be between 1 and 5, in particular between 2 and 4.

The desired product of the coupling reaction can be isolated and purified by conventional separation/purification methods used in the synthetic organic chemistry, such as filtration, extraction, washing, drying, concentration, recrystallization, various chromatographic techniques or the like.

The compounds of the invention are stable and are soluble either in aqueous or organic solvent.

Another object of the present invention relates to the use of at least one compound of formula (I) according to the invention or a compound of formula

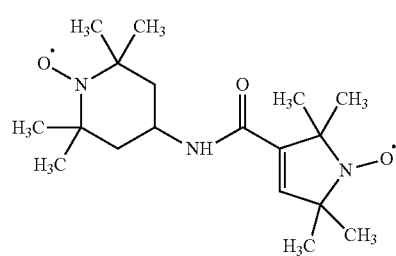

as a polarizing agent.

Another object of the invention relates to the use of at least one compound of formula (I) according to the invention or a compound of formula

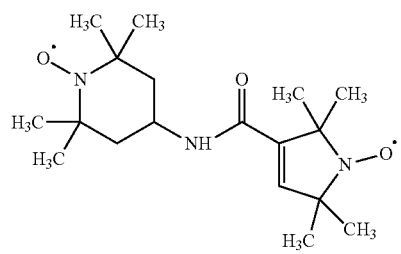

as a polarizing agent in the techniques of structural biology, Nuclear Magnetic Resonance (NMR) of solids or applied to liquid samples, particle physics, and medical imaging. In particular, the compounds according to the invention or a compound of formula

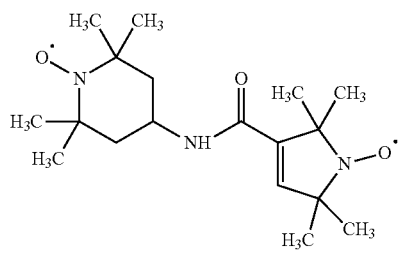

may be used as DNP agents for polarizing an NMR-active isotope of a nucleus in Nuclear Magnetic Resonance (NMR) spectroscopy. The term NMR spectroscopy, as used herein, encompasses Solid State NMR (SS-NMR) spectroscopy, liquid state NMR spectroscopy and Magnetic Resonance Imaging (MRI), in all of which the biradical compounds of the invention may be used as DNP agents.

A nucleus having an NMR-active spin may be, for example: $^1H$, $^2H$, $^6Li$, $^7Li$, $^{10}B$, $^{11}B$, $^{13}C$, $^{14}N$, $^{15}N$, $^{17}O$, $^{19}F$, $^{23}Na$, $^{25}Mg$, $^{27}Al$, $^{29}Si$, $^{31}P$, $^{33}S$, $^{35}Cl$, $^{37}Cl$, $^{39}K$, $^{41}K$, $^{43}Ca$, $^{47}Ti$, $^{49}Ti$, $^{50}V$, V, $^{53}Cr$, $^{77}Se$, $^{89}Y$, $^{117}Sn$, $^{119}Sn$ and $^{199}Hg$.

A further object of the invention relates to a method for polarizing a compound in a sample for Dynamic Nuclear Polarization comprising contacting said sample with at least one compound of formula (I) according to the invention.

The method for polarizing a compound in a sample for Dynamic Nuclear Polarization according to the invention comprises the steps of:

a) providing said at least one compound of formula (I) or a compound of formula

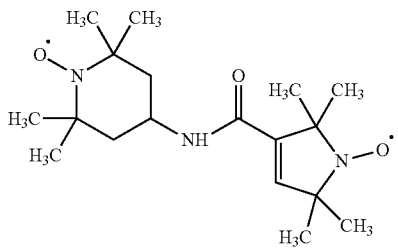

as polarizing agent that enables an optimal nuclear polarization of the sample in a magnetic field;
b) irradiating said sample comprising the compound of formula (I) or a compound of formula

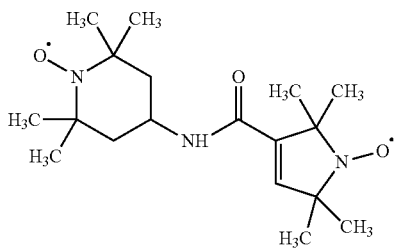

with at least one radiation that causes electron spin flip, to enhance the performance of NMR detection or MRI performance; and
c) optionally dissolving the sample and obtaining a hyperpolarized sample.

Said method may further comprise observing the NMR or MRI of the hyperpolarized compound of formula (I).

The irradiation is preferably a microwave irradiation. The frequency range of the microwave irradiation by which the polarization is transferred to an NMR-active nucleus is usually from 5 to 800 GHz.

The term "sample", as used herein, refers to a chemical or a biological entity, such as a solid inorganic, organic or metallo-organic material having a crystal lattice or an amorphous solid structure (e.g. zeolites, nanoparticles, mesoporous and porous materials, glasses, Metal Organic Frameworks (MOF), a molecular chemical or biochemical compound including polymeric compounds and macromolecular compounds (e.g. proteins, enzymes, DNA/RNA and a biological entity (e.g. a whole cell, a leaf, a virus particle, tissue or bone components or a whole body, having one or more NMR-active spins to be investigated by NMR spectroscopy. The chemical or a biological entity may be isolated or in its natural environment. The sample may be dissolved in aqueous medium, an organic solvent or a mixture of organic or aqueous/organic solvents. The sample may be without a solvent.

The investigation by NMR spectroscopy may be structure determination, monitoring of reaction kinetics, flow imaging, etc.

The polarizing agent may be dissolved in the solvent of the sample or can be chemically bound to the sample and be introduced without a solvent.

The polarizing agent may be present in a solid state, with or without a solvent or mixture of solvents (e.g. frozen solvent(s)), during the polarization time.

The polarizing agent may be present in a liquid state or in a liquid solution during the polarization time.

A compound of formula (I) according to the invention or a compound of formula

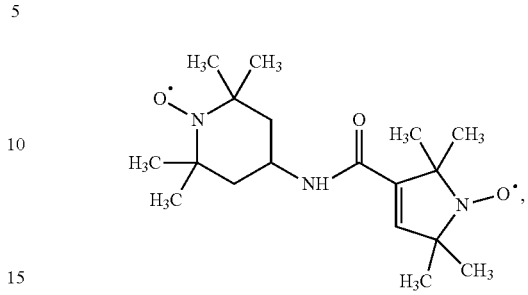

when used as a polarizing agent, is used at a concentration of 0.01 to 200 mM.

In solid state NMR experiments, the temperature of a sample including the polarizing agent is in the range of 1 to 300 K.

The invention will be further illustrated by the following figures and examples. These examples and figures should not in any way be interpreted as limiting the scope of the present invention.

FIGURES

Figure 2:
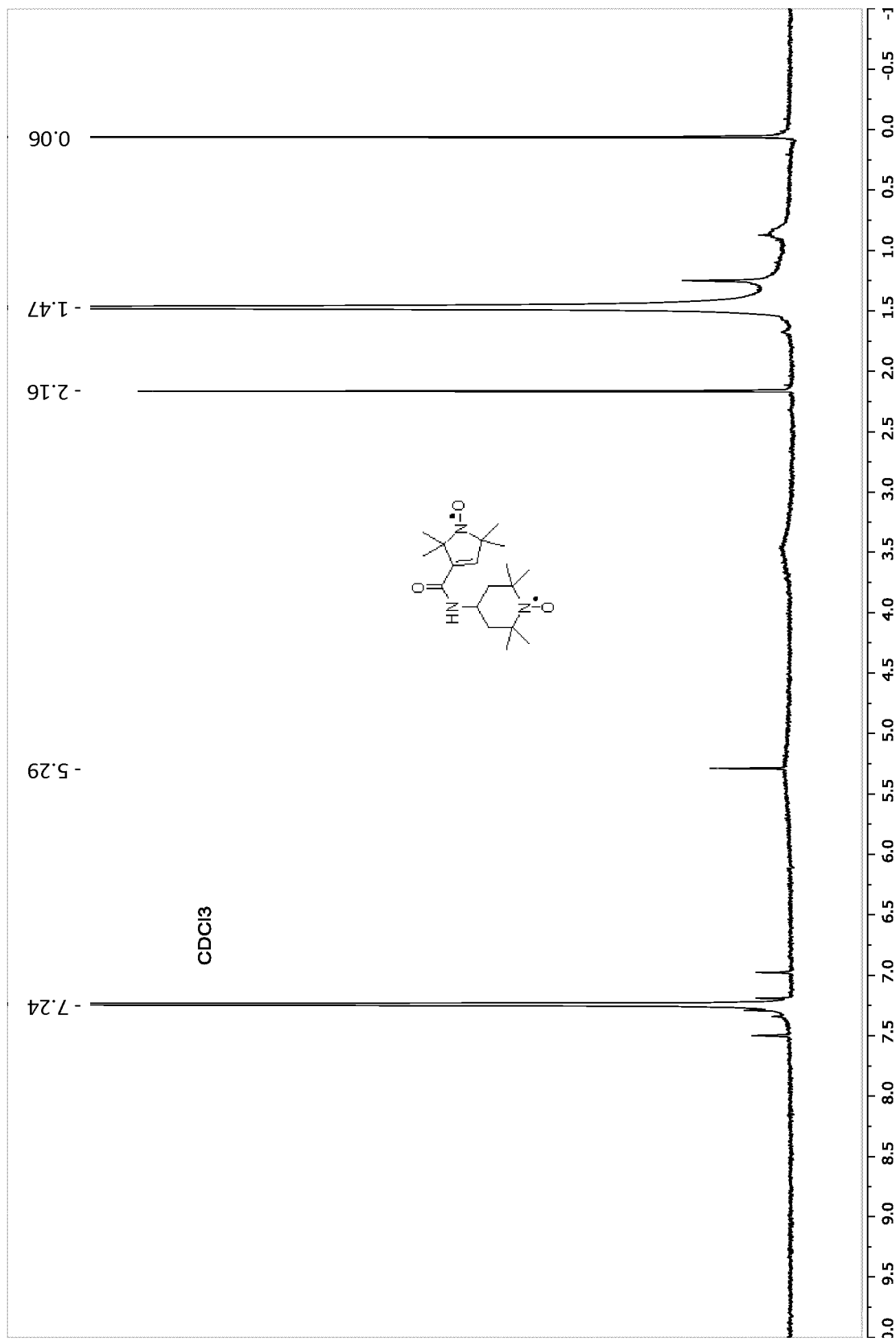
Figure 3:
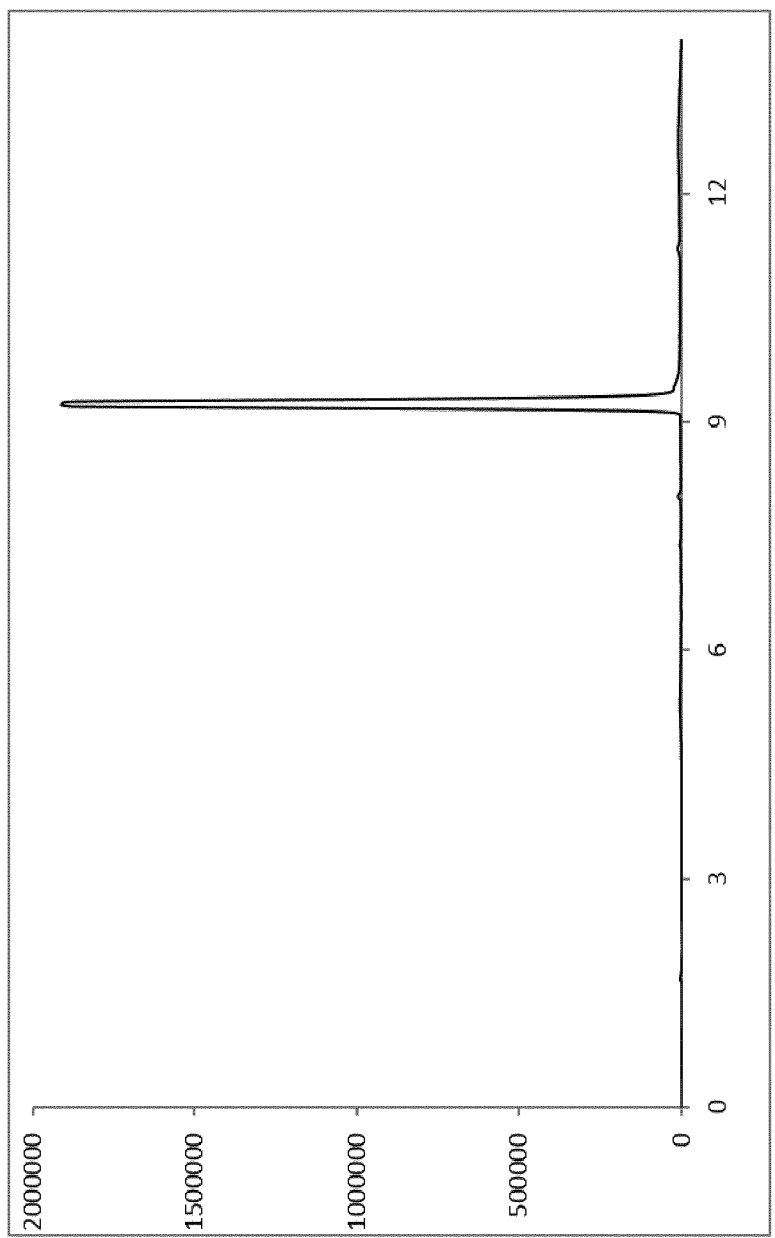
Figure 4:
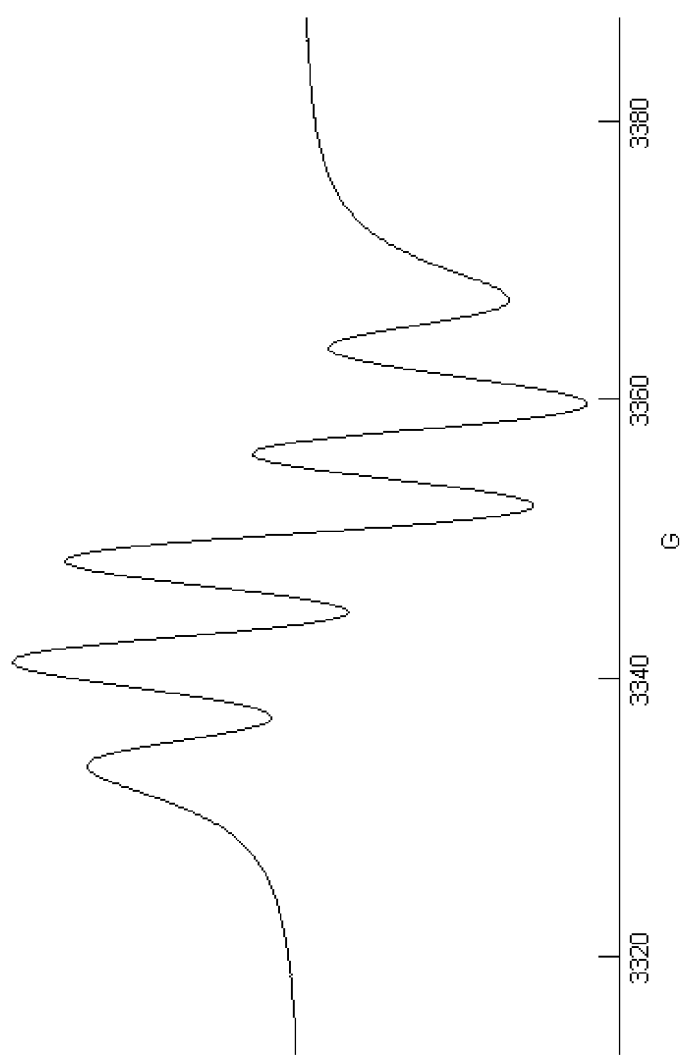
Figure 5:
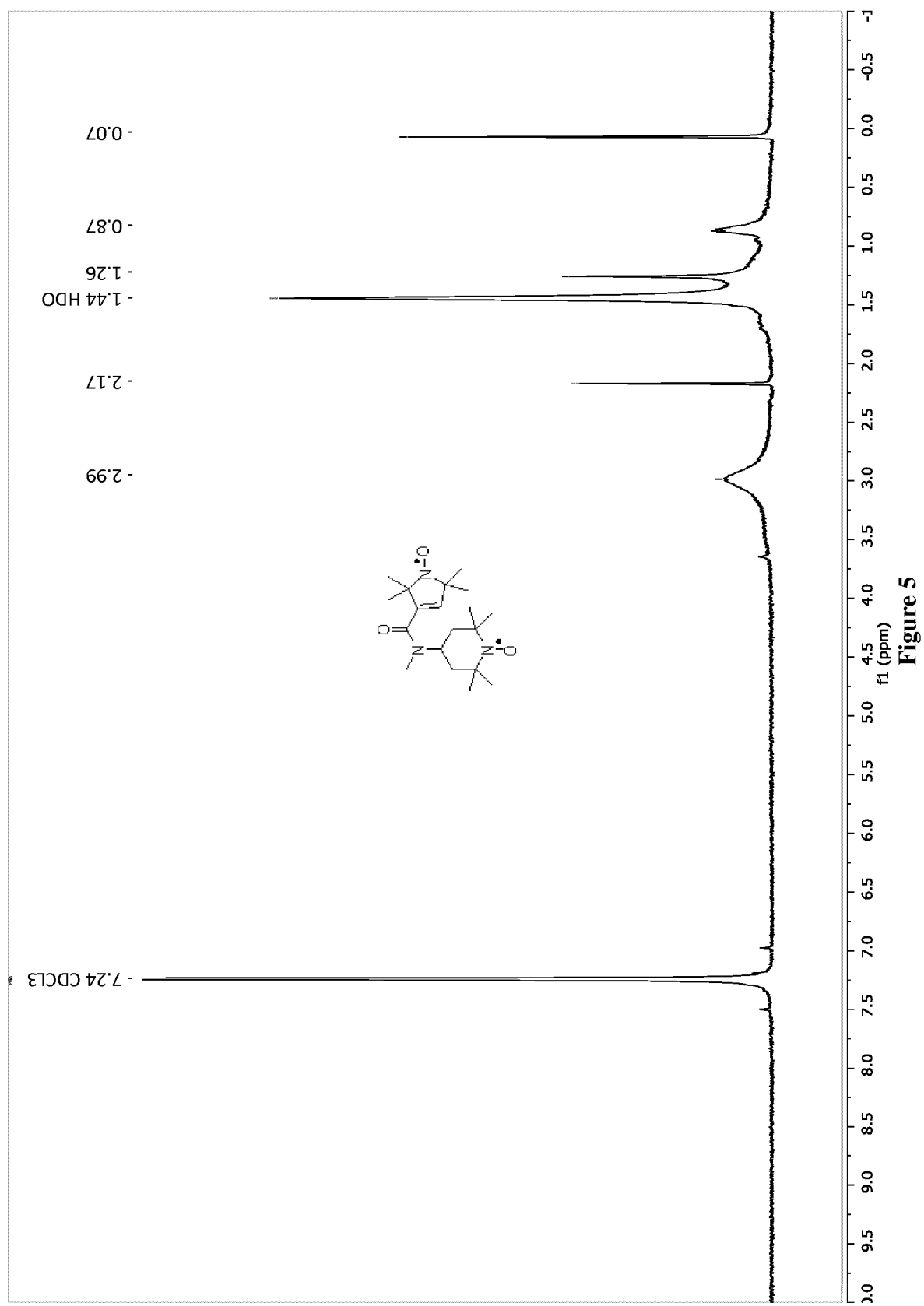
Figure 6:
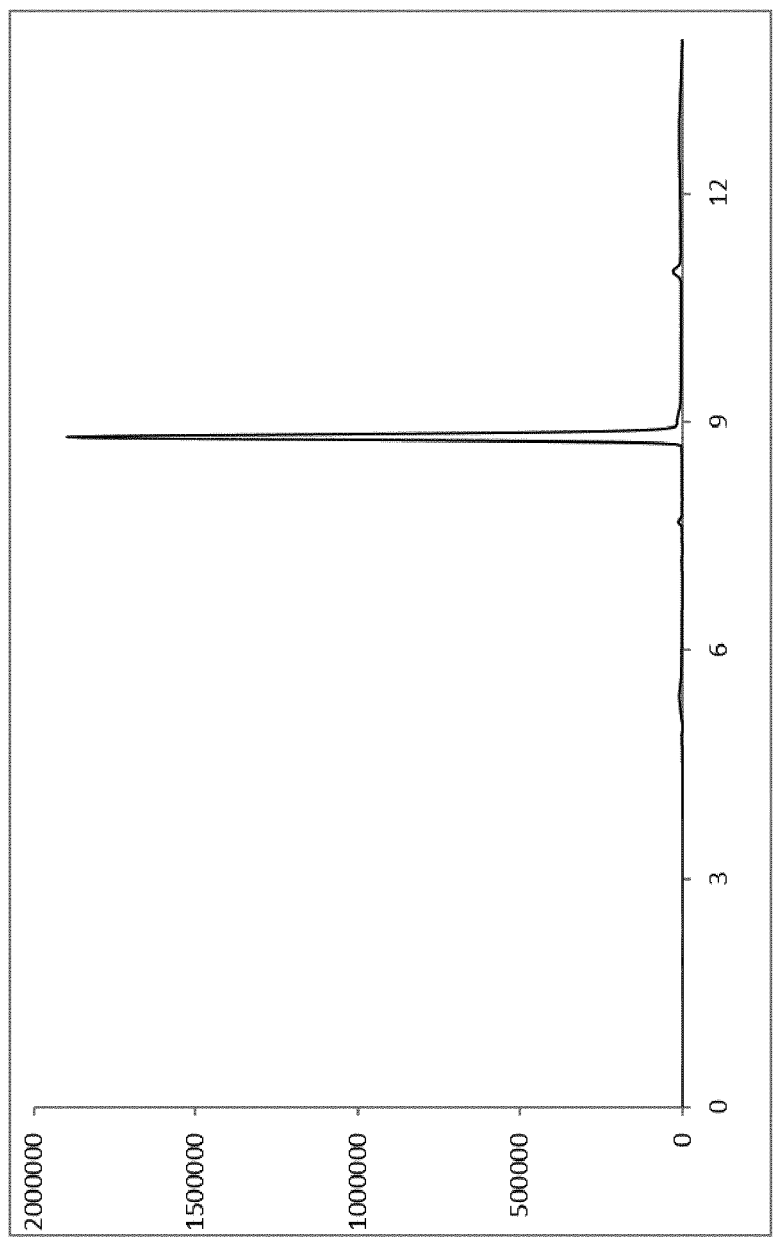
Figure 7:
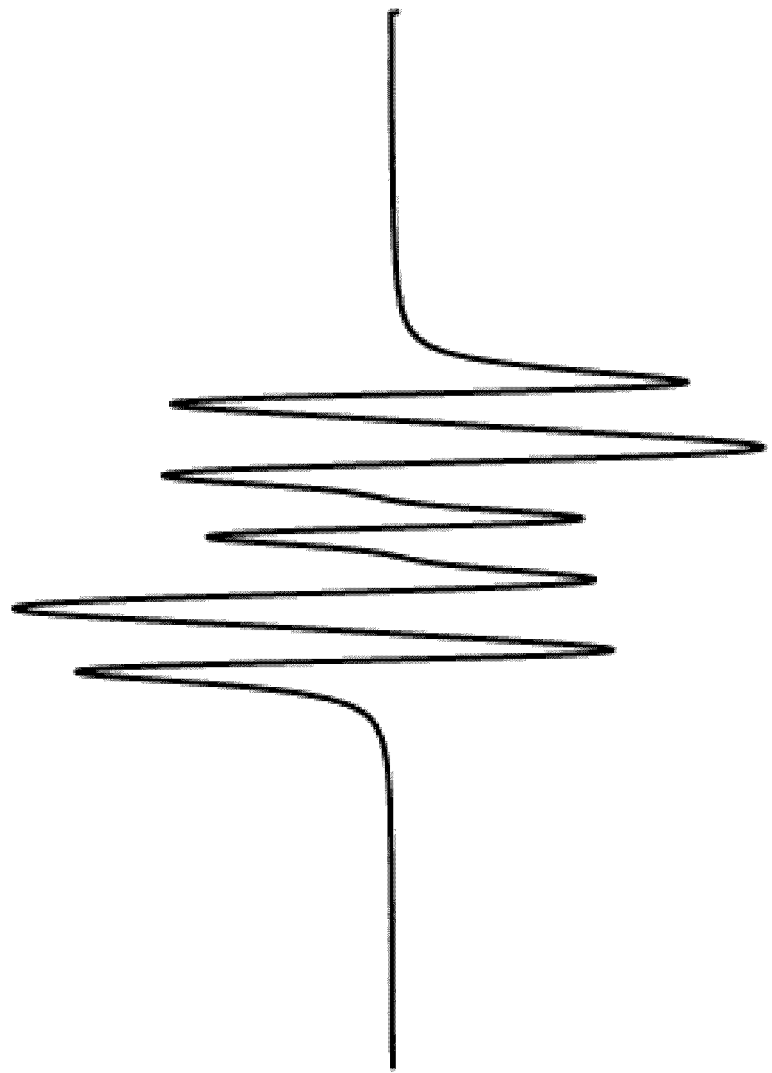
Figure 8:
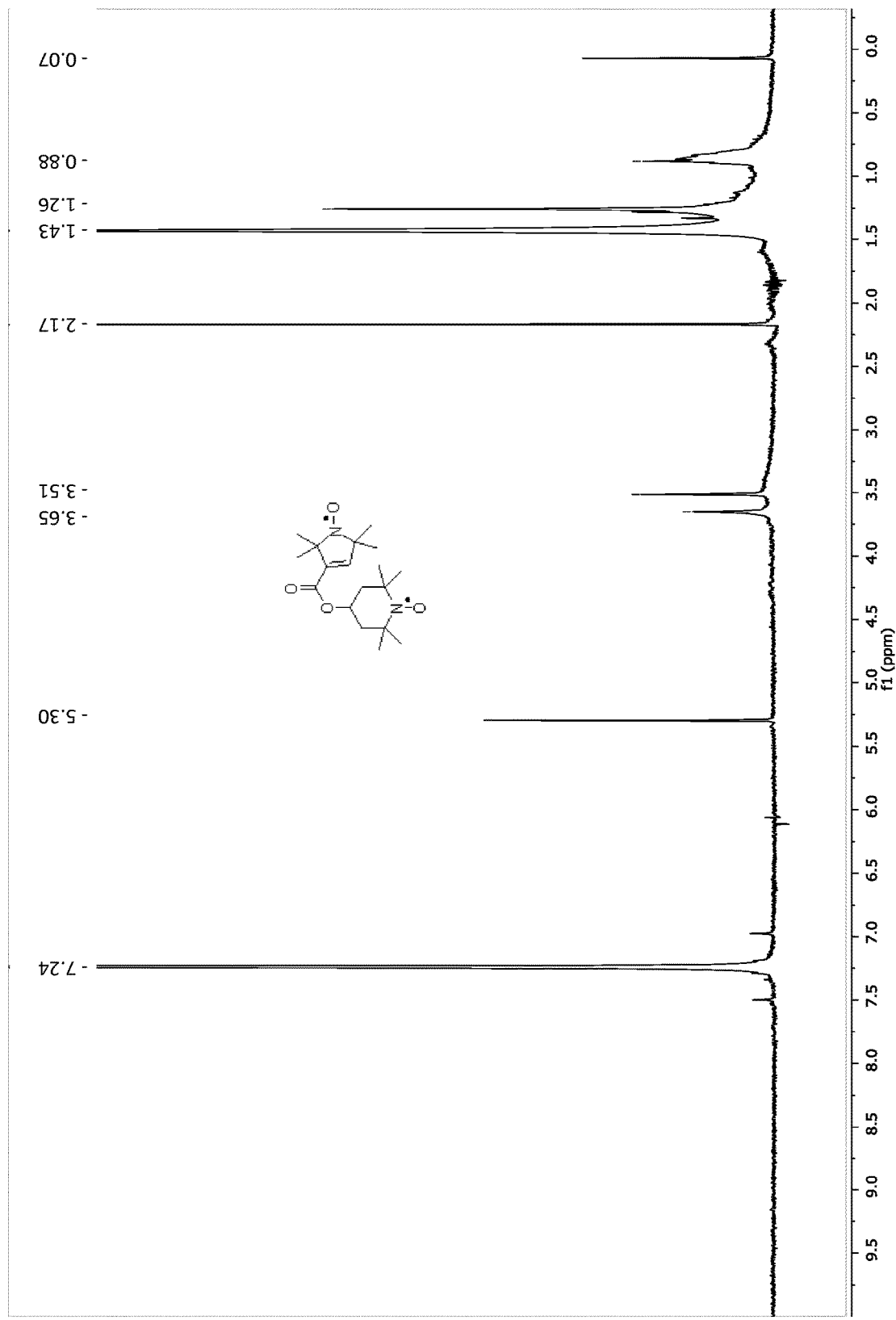
Figure 9:
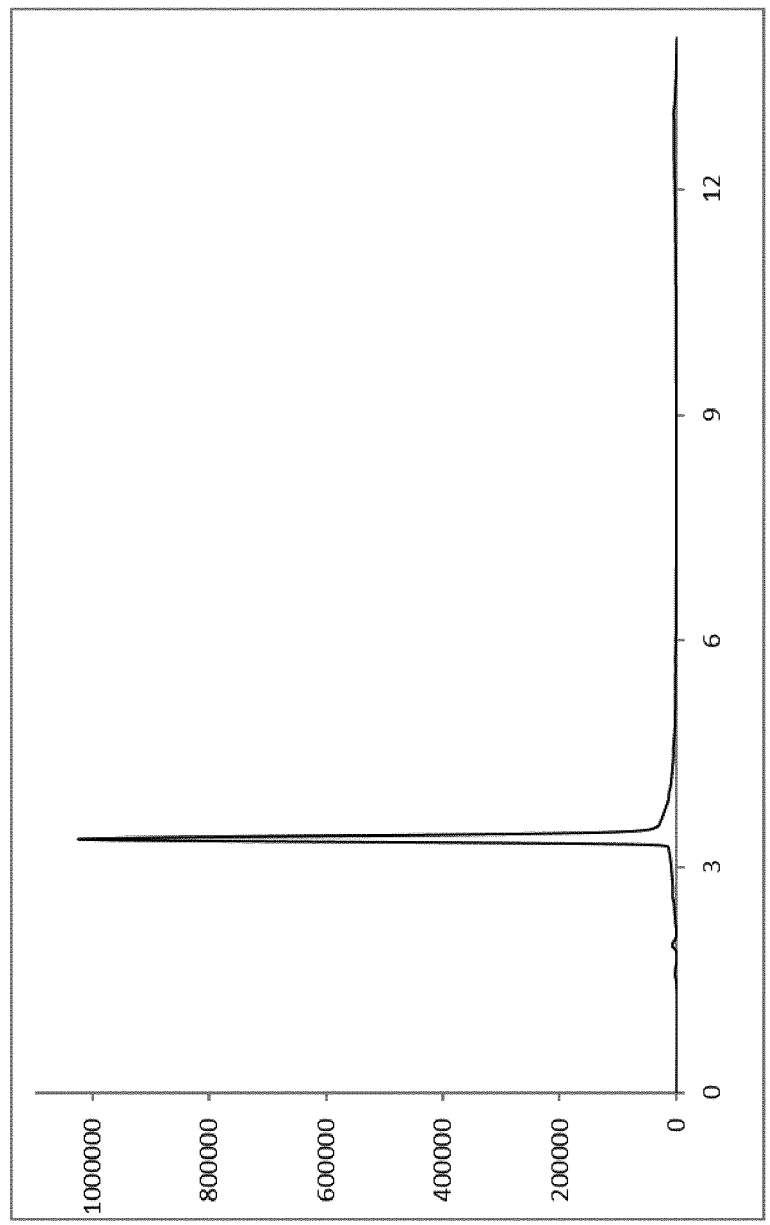
Figure 10:
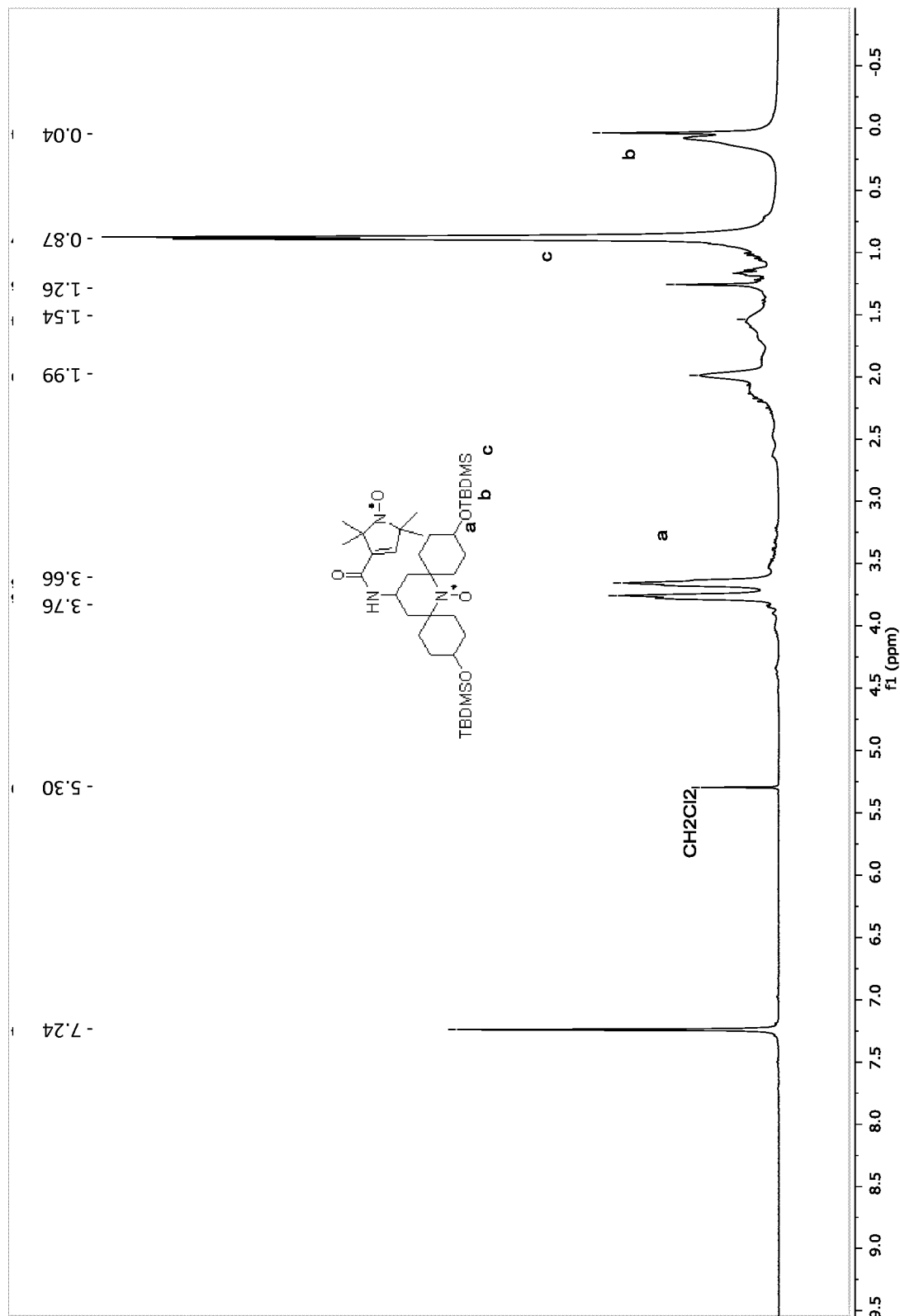
Figure 11:
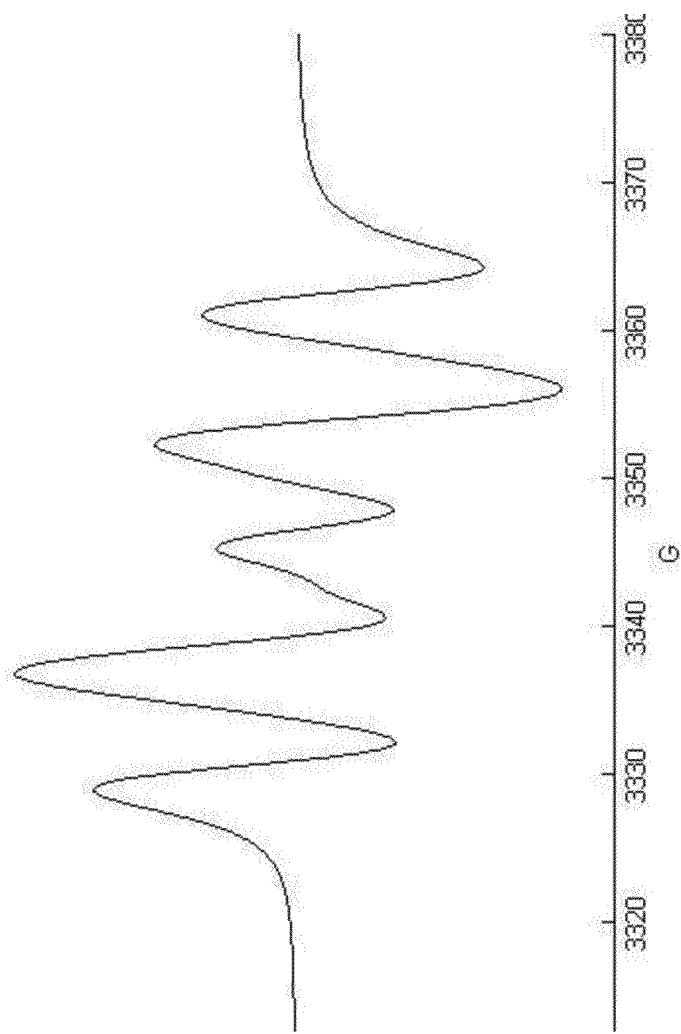
Figure 12:
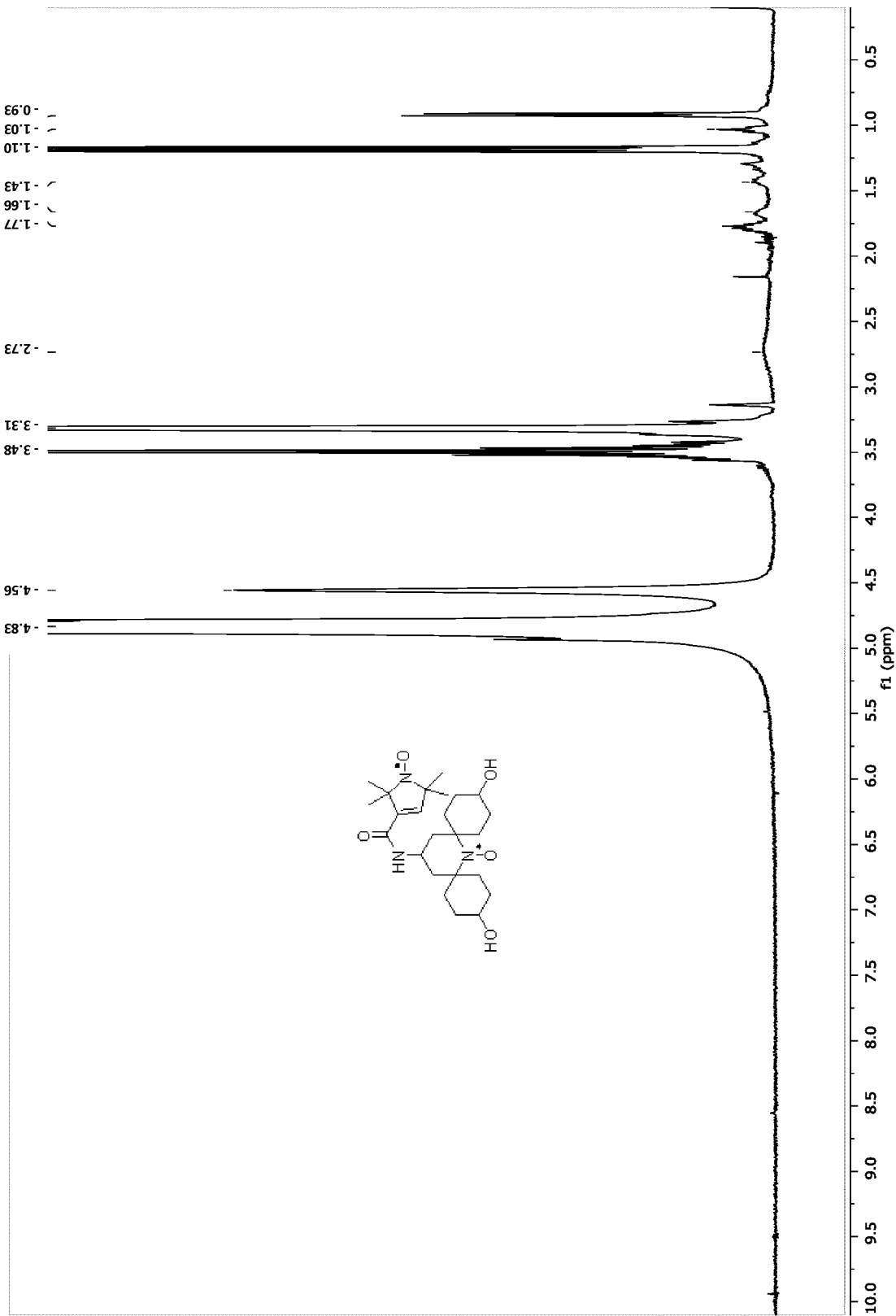
Figure 13:
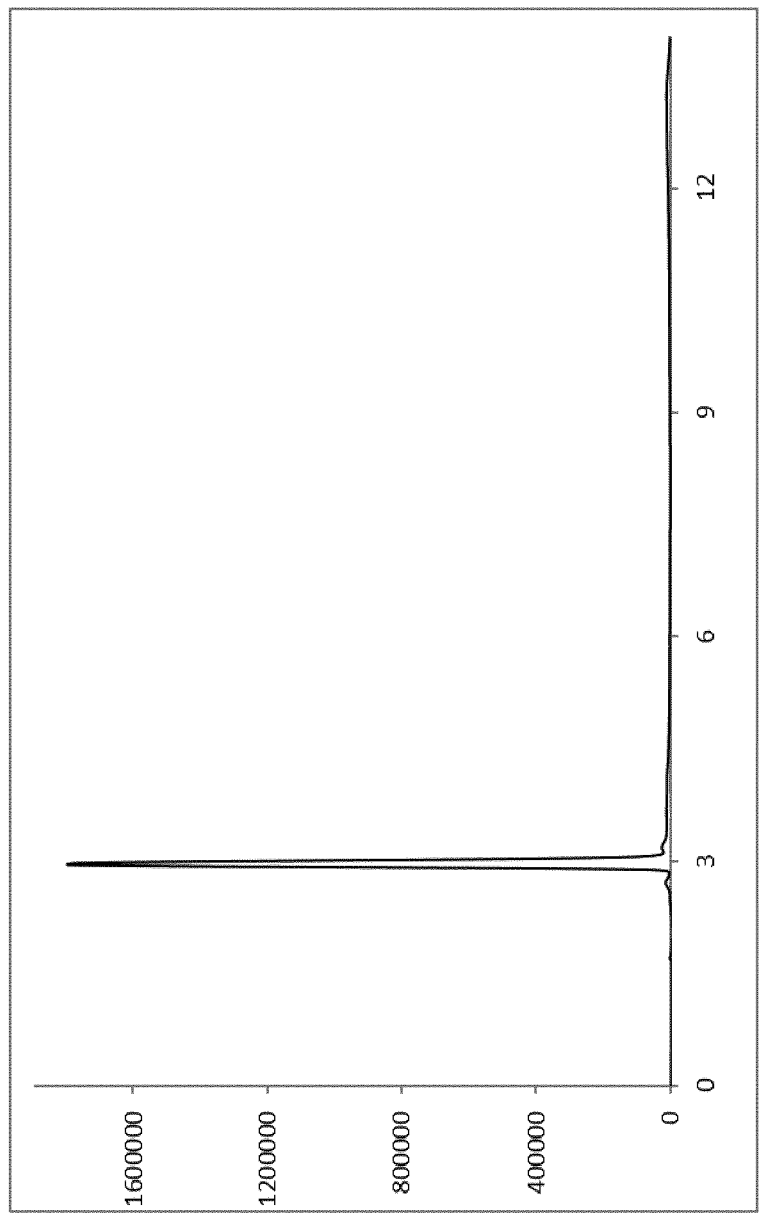
Figure 14:
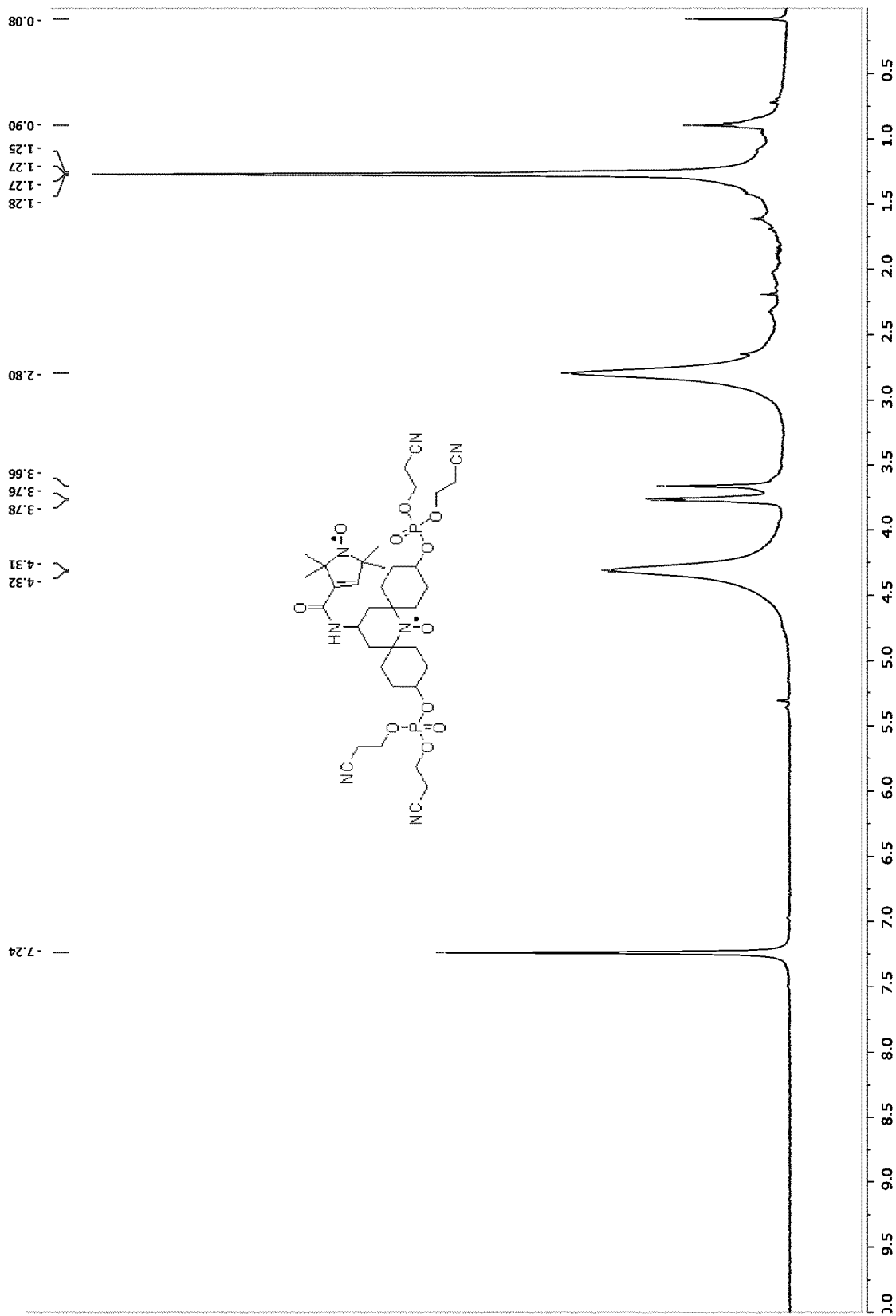
Figure 15:
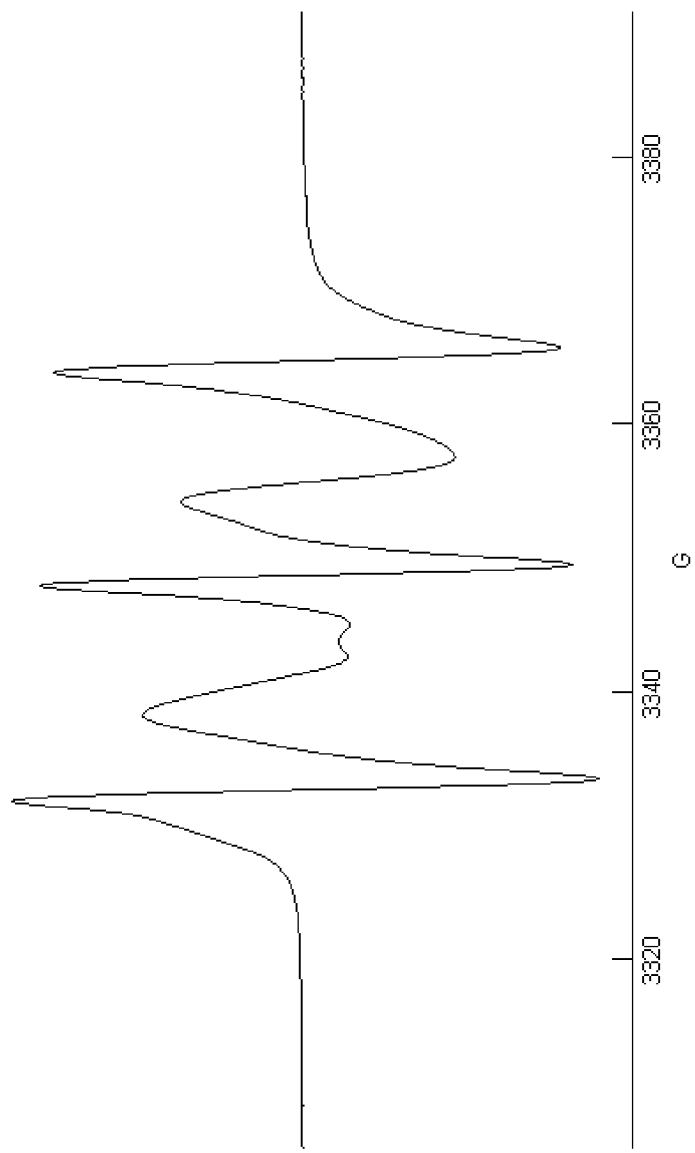
Figure 16:
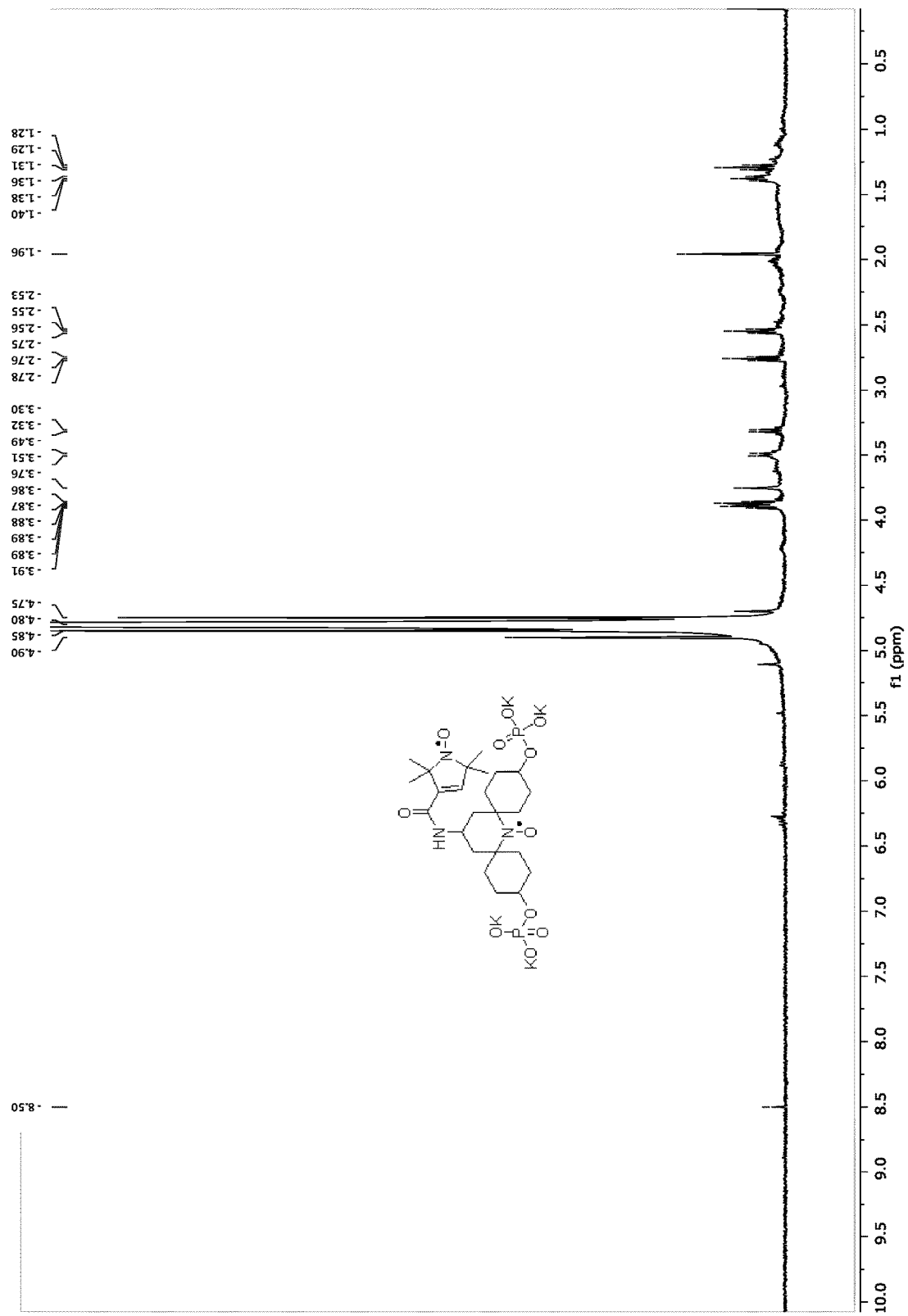
Figure 17:
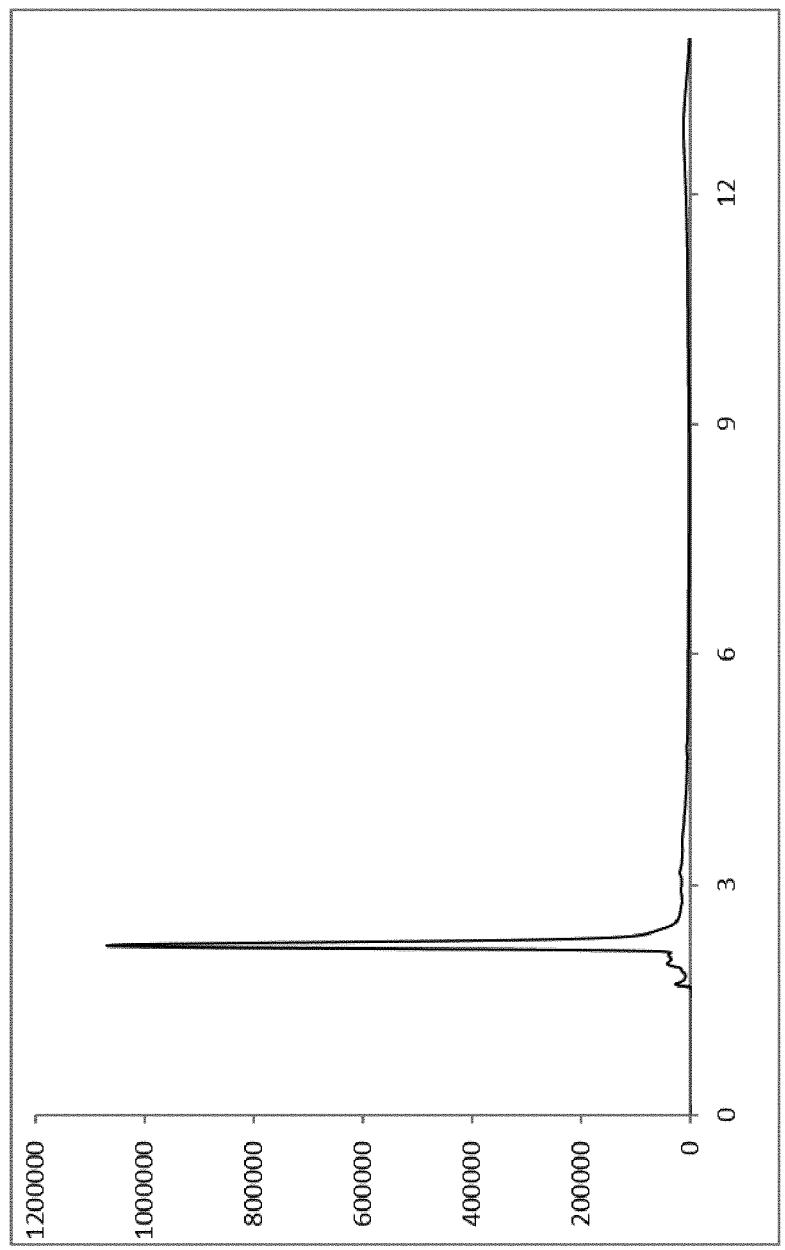

FIG. 1 represents the EPR spectrum of Compound 3, in $CH_2Cl_2$ (1 mM) at 25° C.
FIG. 2 represents the $^1$H-NMR of Compound 3 in $CDCl_3$.
FIG. 3 represents the HPLC chromatogram of Compound 3.
FIG. 4 represents the EPR spectrum of Compound 5, in $CH_2Cl_2$ (1 mM) at 25° C.
FIG. 5 represents the $^1$H-NMR of Compound 5 in $CDCl_3$.
FIG. 6 represents the HPLC chromatogram of Compound 5.
FIG. 7 represents the EPR spectrum of Compound 7, in $CH_2Cl_2$ (1 mM) at 25° C.
FIG. 8 represents the $^1$H-NMR of Compound 7 in $CDCl_3$.
FIG. 9 represents the HPLC chromatogram of Compound 7.
FIG. 10 represents the $^1$H-NMR of Compound 9 in $D_2O$.
FIG. 11 represents the EPR spectrum of Compound 10, in water (1 mM) at 25° C.
FIG. 12 represents the $^1$H-NMR of Compound 10, in $D_2O$.
FIG. 13 represents the HPLC chromatogram of Compound 10.
FIG. 14 represents the $^1$H-NMR of Compound 13 in $CDCl_3$.
FIG. 15 represents the EPR spectrum of Compound 14, in water (1 mM) at 25° C.
FIG. 16 represents the $^1$H-NMR of Compound 14 in in $D_2O$.
FIG. 17 represents the HPLC chromatogram of Compound 14.

EXAMPLES

1/ Synthesis of the AsymPol Biradical Family

Chemicals were purchased primarily from the Sigma-Aldrich Chemical Company and Acros and were used without further purification. Dichloromethane, acetonitrile and pyridine were freshly distilled over calcium hydride before use; triethylamine was purchased anhydrous and stored over potassium hydroxide pellets. Thin layer chromatography (TLC) was performed on glass backed TLC plates with extra hard layer (Kieselgel 60 $F_{254}$, 250 μm, Silicycle) and compounds were visualized by UV light. Silica gel (230-400 mesh, 60 Å) was purchased from Silicycle, and used for flash chromatography. $^{1}$H and $^{13}$C NMR spectra were recorded at the frequencies stated, using deuterated solvents as internal standards. 400 MHz spectra were recorded on a Bruker Advance 400 spectrometer. Residual proton signals from the deuterated solvents were used as references [$D_2O$ (4.81 ppm), $d_6$-DMSO (2.50 ppm), chloroform (7.26 ppm), $d_4$-MeOH (4.84 and 3.31 ppm)] for 1H spectra. The residual $^{13}$C signals from the deuterated solvents being used as references [$d_6$-DMSO (39.7 ppm), chloroform (77.0 ppm), $d_4$-MeOH (49.05 ppm)] for $^{13}$C spectra. All coupling constants were measured in Hertz. All moisture sensitive reactions were carried out in oven-dried glassware using nitrogen or argon from standard BOC industrial cylinders, dried through an activated silica column. Molecular mass of the new organic compounds was determined by HR-ESI/ESI-MS (Bruker, MicroTof-Q). Purity of 3, 5, 10 and 14 were analysed on GL Sciences Inertsustain C18 4.6×150 mm analytical column with UV detection at 254 nm on Beckman Coulter Gold HPLC system. Analytical HPLC run (Flow rate=1 mL/min): Solvent A, 0.1% TFA in water; Solvent B, MeOH; 8 min linear gradient from 0% to 100% B, 2 min linear gradient from 100% to 0% B (initial conditions; 100% A).

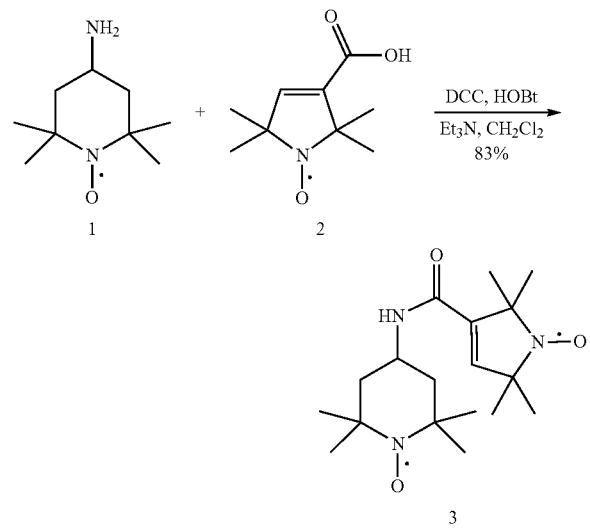

Compound 3:
To a solution of 2 (K. Oyaizu, T. Kawamoto, T. Suga and H. Nishide, *Macromolecules,* 2010, 43, 10382-10389) (0.032 g, 0.175 mmol) in $CH_2Cl_2$ (4 mL) was added DCC (0.039 g, 0.192 mmol), HOBt (0.053 g, 0.35 mmol) and triethyl amine (0.073 mL, 0.525 mmol) under an inert atmosphere of argon. After stirring for 15 minutes, 1 (G. M. Rosen, *J. Med. Chem.,* 1974, 17, 358-360) (0.03 g, 0.175 mmol) was added. The resulting solution was stirred for 12 hours at 25° C., diluted with $CH_2Cl_2$ (10 mL) and washed successively with sat. aqueous solution of $NaHCO_3$ (10 mL) and brine (10 mL). The organic layer was concentrated in vacuo and the crude product was purified by flash column chromatography (silica) using a gradient elution (EtOAc: petroleum ether; 0:100 to 30:70) to give 3 (0.049 g, 83% yield) as a yellow solid.

TLC (Silica gel, 10% MeOH in $CH_2Cl_2$), $R_f$(1)=0.2, $R_f$(2)=0.8, $R_f$(3)=0.9, PMA active.
(Silica gel, 2.5% MeOH in $CH_2Cl_2$), $R_f$(3)=0.3
$^{1}$H-NMR ($CDCl_3$): Compound 3 is a nitroxide biradical and hence, shows broadening of peaks. Therefore, integration of the NMR peaks in NMR spectra was not performed.
LCMS: calculated for $C_{18}H_{31}N_3O_3$: 337.2365, found 339.2520 $(M+2H)^{2+}$.

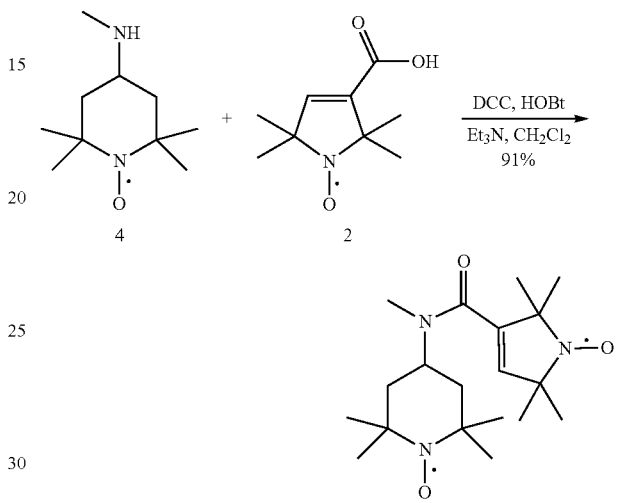

Compound 5:
To a solution of 2 (K. Oyaizu, T. Kawamoto, T. Suga and H. Nishide, *Macromolecules,* 2010, 43, 10382-10389) (0.03 g, 0.162 mmol) in $CH_2Cl_2$ (4 mL) was added DCC (0.037 g, 0.18 mmol), HOBt (0.049 g, 0.32 mmol) and triethyl amine (0.07 mL, 0.495 mmol) under an inert atmosphere of argon. After stirring for 15 minutes, 4 (G. M. Rosen, *J. Med. Chem.,* 1974, 17, 358-360) (0.03 g, 0.162 mmol) was added. The resulting solution was stirred for 12 hours at 25° C., diluted with $CH_2Cl_2$ (10 mL) and washed successively with sat. aqueous solution of $NaHCO_3$ (10 mL) and brine (10 mL). The organic layer was concentrated in vacuo and the crude product which was purified by flash column chromatography (silica) using a gradient elution (EtOAc: petroleum ether; 0:100 to 35:65) to give 5 (0.051 g, 91% yield) as a yellow solid.

TLC (Silica gel, 40% EtOAc in pet ether), $R_f$(2)=0.3, $R_f$(5)=0.2, PMA active. $^{1}$H-NMR ($CDCl_3$): Compound 5 is a nitroxide biradical and hence, shows broadening of peaks. Therefore, integration of the NMR peaks in NMR spectra was not performed.
LCMS: calculated for $C_{19}H_{33}N_3O_3$: 351.2522, found 353.2673 $(M+2H)^{2+}$.

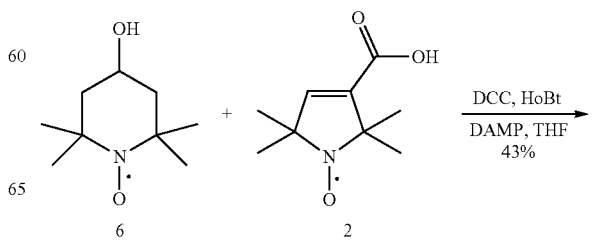

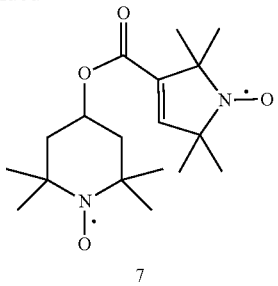

7

Compound 7:

To a solution of 2 (K. Oyaizu, T. Kawamoto, T. Suga and H. Nishide, *Macromolecules*, 2010, 43, 10382-10389) (0.06 g, 0.326 mmol) in THF (6 mL) was added DCC (0.087 g, 0.423 mmol), HOBt (0.057 g, 0.423 mmol) and DMAP (0.23 g, 0.195 mmol) under an inert atmosphere of argon. After stirring for 15 minutes, 6 (0.068 g, 0.390 mmol) was added. The resulting solution was stirred for 12 hours at 25° C. Solvent was removed under vacuo. The residue was diluted with $CH_2Cl_2$ (10 mL) and washed successively with sat. aqueous solution of $NaHCO_3$ (10 mL) and brine (10 mL). The organic layer was concentrated in vacuo and the crude product which was purified by flash column chromatography (silica) using a gradient elution (EtOAc: petroleum ether; 0:100 to 20:80) to give 7 (0.048 g, 43% yield) as a yellow solid.

TLC (Silica gel, 20% EtOAc in pet ether), $R_f$ (2)=0.3, $R_f$ (7)=0.2, PMA active.

$^1$H-NMR ($CDCl_3$): Compound 7 is a nitroxide biradical and hence, shows broadening of peaks. Therefore, integration of the NMR peaks in NMR spectra was not performed.

HRMS: calculated for $C_{18}H_{30}N_2O_4$: 338.4480, found 361.2096 (M+Na)$^+$.

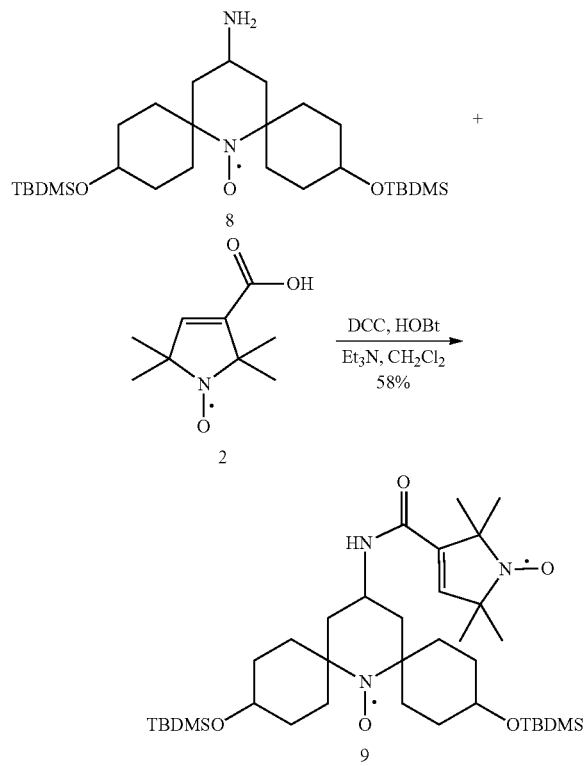

Compound 9:

To a solution of 2 (K. Oyaizu, T. Kawamoto, T. Suga and H. Nishide, *Macromolecules*, 2010, 43, 10382-10389) (0.005 g, 0.029 mmol) in $CH_2Cl_2$ (3 mL) was added DCC (0.006 g, 0.32 mmol), HOBt (0.009 g, 0.059 mmol) and triethylamine (0.013 mL, 0.088 mmol) under an inert atmosphere of argon. After stirring for 15 minutes, 8 (A. P. Jagtap, M. A. Geiger, D. Stöppler, M. Orwick-Rydmark, H. Oschkinat and S. T. Sigurdsson, *Chem. Commun.*, 2016, 52, 7020-7023) (0.015 g, 0.029 mmol) was added. The resulting solution was stirred for 12 hours at 25° C. The reaction mixture was diluted with $CH_2Cl_2$ (10 mL) and washed successively with sat. aqueous solution of $NaHCO_3$ (10 mL) and brine (10 mL). The organic layer was concentrated in vacuo and the crude product which was purified by flash column chromatography (silica) using a gradient elution (EtOAc: petroleum ether; 0:100 to 30:70) to give 9 (0.011 g, 58% yield) as a yellow solid.

TLC (Silica gel, 3% MeOH in $CH_2Cl_2$), $R_f$ (2)=0.3, $R_f$ (9)=0.6, PMA active.

$^1$H-NMR ($CDCl_3$): Compound 9 is a nitroxide biradical and hence, shows broadening of peaks. Therefore, integration of the NMR peaks in NMR spectra was not performed.

HRMS: calculated for $C_{36}H_{67}N_3O_5Si_2$: 677.4619, found 700.4505 (M+Na)$^+$.

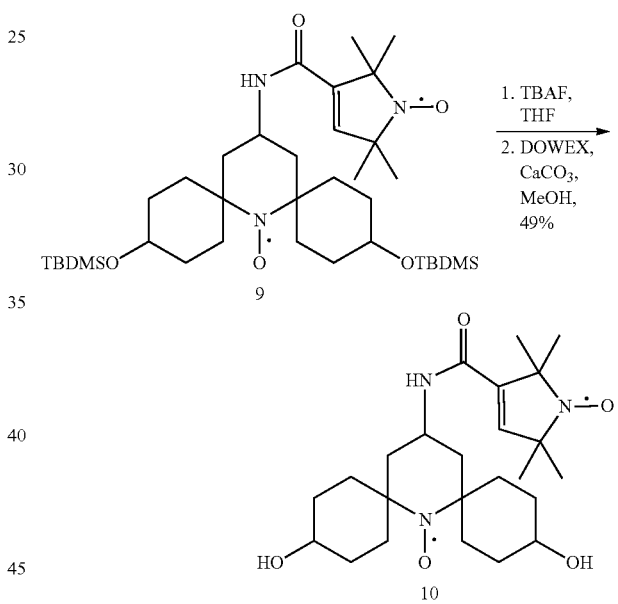

Compound 10:

TBAF (0.8 mL, 0.778 mmol, 1 M in THF) was added to a solution of 9 (0.088 g, 0.130 mmol) in anhydrous THF (4 mL). The resulting solution was heated at 60° C. for 12 hours, cooled down and the solvent removed in vacuo. The residue was dissolved in MeOH (4 mL) and DOWEX (0.50 g) and $CaCO_3$ (0.165 g) were added. The resulting suspension was stirred at for 12 hours at 27° C. The reaction mixture was filtered through a bed of celite, the filtrate concentrated under vacuo and the crude product was purified by flash column chromatography (silica) using a gradient elution (MeOH: $CH_2Cl_2$; 0:100 to 10:90) to give 10 (0.034 g, 49% yield) as a yellow solid.

TLC (Silica gel, 10% MeOH in $CH_2Cl_2$), $R_f$ (12)=1, $R_f$ (10)=0.1, PMA active.

$^1$H-NMR ($D_2O$): Compound 10 is a nitroxide biradical and hence, shows broadening of peaks. Therefore, integration of the NMR peaks in NMR spectra was not performed.

HRMS: calculated for $C_{24}H_{39}N_3O_5$: 449.2890, found 472.2774 (M+Na)$^+$.

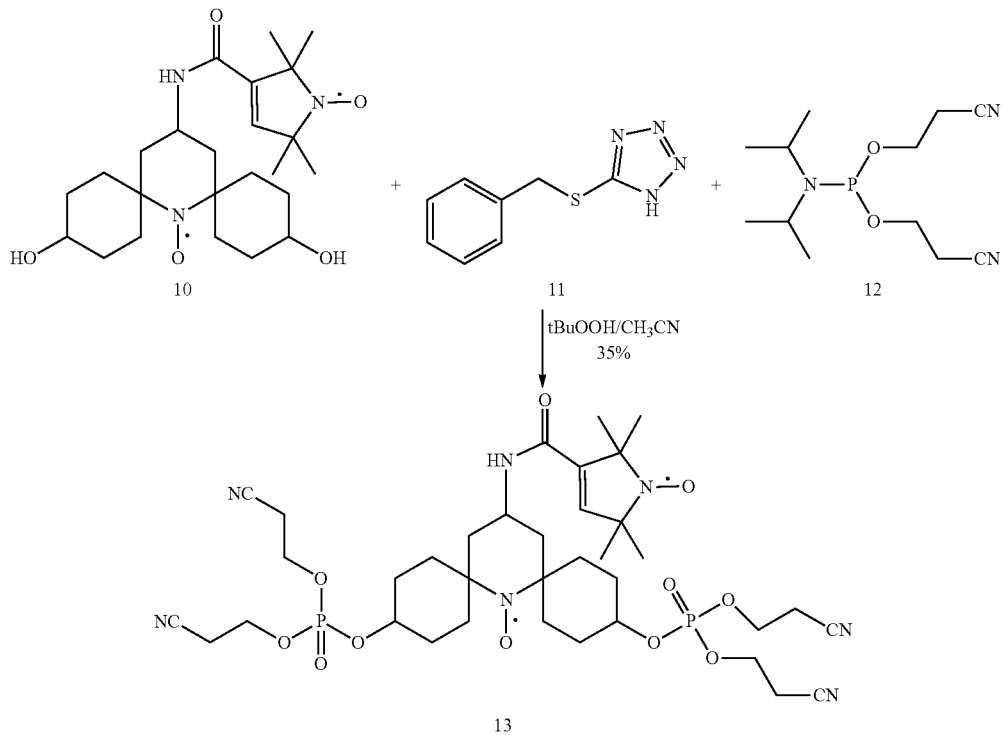

Compound 13:

To a solution of 10 (0.045 g, 0.10 mmol) in CH$_3$CN (4 mL) was added 11 (0.058 g, 0.3 mmol) and 12 (0.053 g, 0.35 mmol) under an inert atmosphere of argon. After stirring for 2 hours at 27° C., tBuOOH (0.384 mL, 3.2 mmol, 75% in water) was added. The resulting solution was stirred for 30 minutes at 25° C. The solvent was removed under vacuo, the residue obtained was diluted with CH$_2$Cl$_2$ (10 mL) and washed successively with sat. aqueous solution of NaHCO$_3$ (10 mL) and brine (10 mL). The organic layer was concentrated in vacuo and the crude product was purified by flash column chromatography (silica) using a gradient elution (MeOH: CH$_2$Cl$_2$; 0:100 to 3:97) to give 13 (0.028 g, 35% yield) as a yellow solid.

TLC (Silica gel, 10% MeOH in CH$_2$Cl$_2$), R$_f$ (10)=0.4, R$_f$ (13)=0.6, PMA active.

$^1$H-NMR (CDCl$_3$): Compound 13 is a nitroxide biradical and hence, shows broadening of peaks. Therefore, integration of the NMR peaks in NMR spectra was not performed.

$^{31}$P-NMR (CDCl$_3$): −3.74, −4.35

HRMS: calculated for C$_{36}$H$_{53}$N$_7$O$_{11}$P$_2$: 821.3278, found 844.3172 (M+Na).

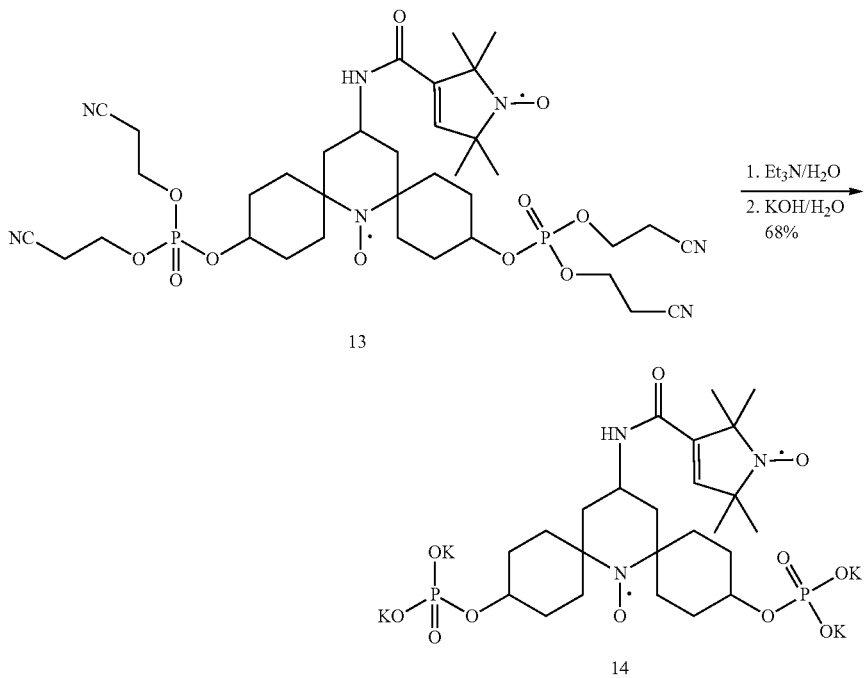

Compound 14:

To a solution of 13 (0.045 g, 0.0739 mmol) in H$_2$O (2 mL) was added triethylamine (0.3 mL, 2.143 mmol). The resulting solution was stirred for 12 hours at 60° C. The solvent was removed in vacuo. The residue was diluted with H$_2$O (2 mL) and KOH (0.018 g, 0.325 mmol) was added. The resulting solution was stirred for 12 hours at 60° C. The solvent was removed in vacuo to give 14 (0.038 g, 68% yield) as a yellow solid.

TLC (Silica gel, 10% MeOH in CH$_2$Cl$_2$), R$_f$(13)=0.6, R$_f$(14)=0, PMA active.

$^1$H-NMR (D$_2$O): Compound 14 is a nitroxide biradical and hence, shows broadening of peaks. Therefore, integration of the NMR peaks in NMR spectra was not performed.

$^{31}$P-NMR (D$_2$O): −3.23

HRMS: calculated for C$_{24}$H$_{41}$N$_3$O$_{11}$P$_2$: 609.2216, found 630.1948 (M+Na-2H).

2/ Sensitivity of the Compounds According to the Invention Under DNP Conditions

The table below compares the sensitivity gain ($\varepsilon_B/\sqrt{T_B}$) obtained with a compound according to the invention, AsymPol, AsymPolPOK and AMUPol which is currently considered as one of the best performing polarizing agent for MAS-DNP experiments.

TABLE 1

Experimental parameters that characterize the DNP performance of AsymPol and AsymPolPOK, with a comparison to AMUPol.

| 9.4 T | DNP sensitivity $\varepsilon_B \cdot T_{B(MAS)}^{-1/2}$ | DNP gain $\varepsilon_{B(MAS)}$ | Buildup Time T$_B$ | | $\varepsilon_{on/off}$ | |
|---|---|---|---|---|---|---|
| | | | Static | MAS | Static | MAS |
| AMUPol[a] | 27 s$^{-1/2}$ | 43 | 16.3 s | 2.5 s | 28 | 151 |
| AsymPol[b] | 39 s$^{-1/2}$ | 30 | 1.0 s | 0.6 s | 11 | 32 |
| AsymPolPOK[a] | 68 s$^{-1/2}$ | 83 | 3.5 s | 1.5 s | 25 | 105 |

[a]10 mM biradical in d$_8$-glycerol/D$_2$O/H$_2$O (6:3:1; v:v) with 20 mM $^{13}$C-urea, 10 kHz MAS rate, at 105K and 9.4 T.
[b]same as [a] but 10 mM biradical in d$_6$-DMSO/D$_2$O/H$_2$O (8:1:1; v:v).
[c]same as [a] but at ~130K and 8 kHz MAS rate using a 3.2 mm rotor.

It appears clearly from these results that the use of AsymPol biradicals provides a significant increase in DNP sensitivity compared to AMUPol. These results also illustrate the limits of relying solely on $\varepsilon_{on/off}$ to evaluate polarizing agent's efficiency.

3/ Characteristics of the Compounds According to the Invention

Table 2 compares certain characteristics of the known polarizing agents, i.e. TOTAPOL, AMUPol and TEKPol.

TABLE 2

| Characteristics | AsymPol | TOTAPOL | AMUPol («bTurea» family) | TEKPol («bTbK» family) |
|---|---|---|---|---|
| Spin interaction | intense | moderate | moderate to intense | moderate |
| Relative orientations of the g tensor | rigid | flexible | rigid | very rigid |
| Amplification factor $\varepsilon_{on/off}$ (for 10 mM biradicals) | important | moderate | important to very important | important to very important |
| Depolarization strength | Weak (almost absent) | moderate | strong | moderate to strong |
| Polarization speed | very fast | slow | fast | moderate |
| Sensitivity gain | very high | moderate | moderate to important | moderate to important |
| Efficiency et high MAS frequency (>20 kHz) | good | weak | weak to moderate | weak |

The table above illustrates the reason for which the polarizing agents proposed up to now offer modest performances (especially at high spinning frequencies).

The invention claimed is:

1. A compound of formula (I)

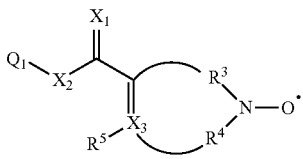
(I)

wherein
$X_1$ is O;
$X_2$ is O, or —$NR^9$;
$X_3$ is C;
$R^5$ is H;
$R^9$ is H; a substituted or unsubstituted, linear, branched or cyclic $C_{1-6}$ aliphatic group; —$(CH_2)_n$—COOH with n being an integer from 1 to 10, —OH, —$NH_2$, —$N_3$, —C≡CH, $P(O)(OH)_2$, $P(O)(OR^{11})_2$, $P(O)R^{11}_2$, $SSO_2Me$, —$(CH_2$—$CH_2$—$O)_m$—$CH_3$ or —$(CH_2$—$CH_2$—$O)_m$—H with m being an integer from 1 to 500, or

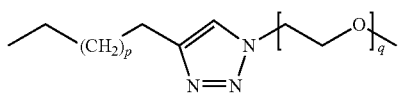

with p being an integer from 0 to 7 and q an integer from 1 to 500;
$Q_1$ is a cyclic nitroxide radical, as represented below

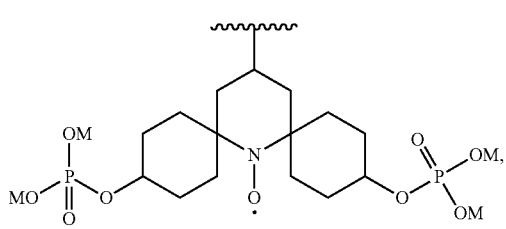

wherein M is an alkali metal selected in the group consisting of lithium (Li), sodium (Na), potassium (K), rubidium (Rb) and cesium (Cs); and
$R^3$ and $R^4$ are joined, through the double bond C≡$X_3$ to form together with the nitrogen atom to which they are bound a 5-membered heterocyclic ring selected from

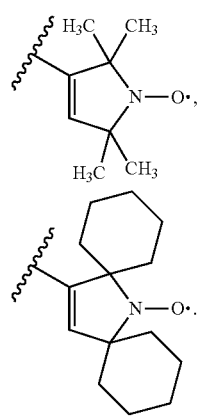

2. The compound of formula (I) according to claim 1, wherein M is lithium (Li), sodium (Na), or potassium (K).

3. The compound of formula (I) according to claim 1, wherein $X_2$ is O or —$NR^9$ wherein $R^9$ is H; a substituted or unsubstituted, linear, branched or cyclic $C_{1-6}$ alkyl group; —$(CH_2)_n$—COOH with n being an integer from 1 to 10, —$(CH_2$—$CH_2$—$O)_m$—$CH_3$ or —$(CH_2$—$CH_2$—$O)_m$—H with m being an integer from 1 to 500.

4. The compound of formula (I) according to claim 1, wherein $X_2$ is O or —$NR^9$ wherein $R^9$ is H, a linear or branched $C_{1-6}$ alkyl, —$(CH_2$—$CH_2$—$O)_m$—$CH_3$ with m being 1 to 10.

5. A compound represented as below:

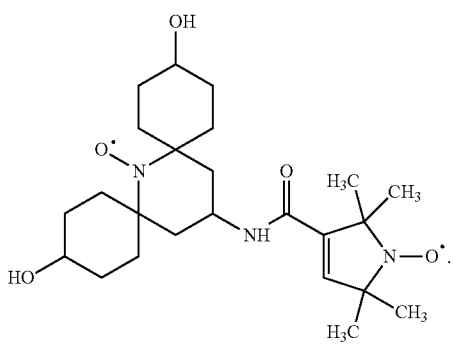

AsymPol II

6. A compound represented as below:

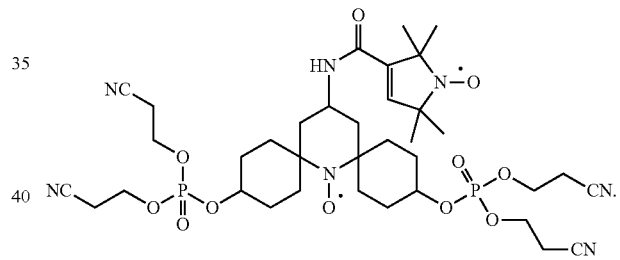

7. A compound represented as below:

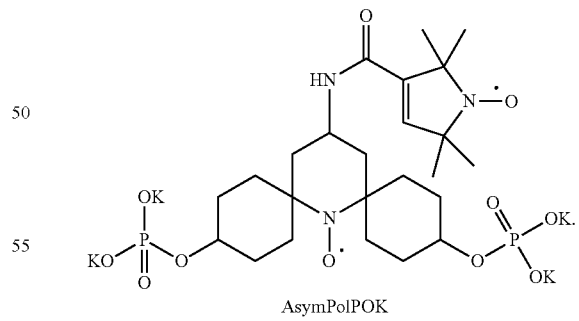

AsymPolPOK

8. A method for polarizing a compound in a sample for Dynamic Nuclear Polarization, wherein said method comprises the steps of:
a) providing at least one compound of formula (I) according to claim 1 as polarizing agent that enables an optimal nuclear polarization of a sample in a magnetic field;
b) irradiating said sample comprising the compound of formula (I) with at least one radiation that causes electron spin flip, to enhance the performance of NMR detection or MRI performance; and c) optionally dissolving the sample and obtaining a hyperpolarized sample.

* * * * *